(12) United States Patent
Foley et al.

(10) Patent No.: US 7,862,595 B2
(45) Date of Patent: *Jan. 4, 2011

(54) INSTRUMENTS AND METHODS FOR STABILIZATION OF BONY STRUCTURES

(75) Inventors: Kevin T. Foley, Germantown, TN (US); Michael C. Sherman, Memphis, TN (US); Jeff R. Justis, Gulf Breeze, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 941 days.

This patent is subject to a terminal disclaimer.

(21) Appl. No.: 11/656,716

(22) Filed: Jan. 23, 2007

(65) Prior Publication Data

US 2007/0185491 A1 Aug. 9, 2007

Related U.S. Application Data

(60) Division of application No. 10/126,237, filed on Apr. 19, 2002, now Pat. No. 7,188,626, which is a continuation-in-part of application No. 09/616,581, filed on Jul. 14, 2000, now Pat. No. 6,530,929.

(60) Provisional application No. 60/186,729, filed on Mar. 3, 2000, provisional application No. 60/160,489, filed on Oct. 20, 1999.

(51) Int. Cl.
*A61B 17/70* (2006.01)
*A61B 17/88* (2006.01)

(52) U.S. Cl. .................. 606/279; 606/246; 606/86 A

(58) Field of Classification Search .................. 606/246, 606/261, 264–267, 270, 272, 278, 279, 301, 606/307, 308, 99, 102, 104, 86 A; 604/170.03; 403/2, 6–10, 13, 14, 19, 90, 122; 411/2, 411/3, 393

See application file for complete search history.

(56) References Cited

U.S. PATENT DOCUMENTS

| 2,338,159 A | 1/1944 | Appleton |
| 2,372,866 A | 4/1945 | Tofflemire |
| 2,697,433 A | 12/1954 | Zehnder |
| 3,892,232 A | 7/1975 | Neufeld |

(Continued)

FOREIGN PATENT DOCUMENTS

DE 19726754 A1 1/1997

(Continued)

OTHER PUBLICATIONS

Sofamor Danek; The Spine Specialist, TSRH Pedicle Screw Spinal System, Severe Spondylolisthesis of L5-S1 Grade 3 & 4; Surgical Technique as described by Edward H. Simmons, MD, Edward D. Simmons, Jr. MD, Howard D. Markowitz, MD Copyright 1997.

(Continued)

*Primary Examiner*—Eduardo C Robert
*Assistant Examiner*—David Comstock

(57) ABSTRACT

The present invention relates to methods and instruments for placing a brace or connecting element into an animal subject for engagement with anchors secured in the animal subject. The installation instrument includes anchor extensions coupled to the anchors. The instrument is movable with respect to the anchors to position the connecting element in a position more proximate the anchors.

20 Claims, 16 Drawing Sheets

U.S. PATENT DOCUMENTS

| | | |
|---|---|---|
| 4,335,715 A | 6/1982 | Kirkley |
| 4,349,921 A | 9/1982 | Kuntz |
| 4,409,968 A | 10/1983 | Drummond |
| 4,448,191 A | 5/1984 | Rodnyansky et al. |
| 4,501,269 A | 2/1985 | Bagby |
| 4,545,374 A | 10/1985 | Jacobson |
| 4,573,448 A | 3/1986 | Kambin |
| 4,722,331 A | 2/1988 | Fox |
| 4,743,256 A | 5/1988 | Brantigan |
| 4,790,303 A | 12/1988 | Steffee |
| 4,820,305 A | 4/1989 | Harms et al. |
| 4,863,430 A | 9/1989 | Klyce et al. |
| 4,863,476 A | 9/1989 | Shepperd |
| 4,883,048 A | 11/1989 | Purnell et al. |
| 4,896,661 A | 1/1990 | Bogert et al. |
| 4,903,691 A | 2/1990 | Heinl |
| 4,917,704 A | 4/1990 | Frey et al. |
| 4,955,885 A | 9/1990 | Meyers |
| 4,955,908 A | 9/1990 | Frey et al. |
| 4,957,495 A | 9/1990 | Kluger |
| 4,987,892 A * | 1/1991 | Krag et al. ............. 606/264 |
| 5,080,662 A | 1/1992 | Paul |
| 5,092,866 A | 3/1992 | Beard et al. |
| 5,116,344 A | 5/1992 | Sundqvist |
| 5,163,940 A | 11/1992 | Bourque |
| 5,171,279 A | 12/1992 | Mathews |
| 5,196,013 A | 3/1993 | Harms et al. |
| 5,242,443 A | 9/1993 | Kambin |
| 5,242,444 A | 9/1993 | MacMillan |
| 5,281,223 A | 1/1994 | Ray |
| 5,314,429 A | 5/1994 | Goble |
| 5,334,205 A | 8/1994 | Cain |
| 5,342,361 A | 8/1994 | Yuan et al. |
| 5,364,399 A | 11/1994 | Lowery et al. |
| 5,383,454 A | 1/1995 | Bucholz |
| 5,395,372 A | 3/1995 | Holt et al. |
| 5,409,488 A | 4/1995 | Ulrich |
| 5,437,667 A | 8/1995 | Papierski et al. |
| 5,474,551 A | 12/1995 | Finn et al. |
| 5,522,899 A | 6/1996 | Michelson |
| 5,549,612 A | 8/1996 | Yapp et al. |
| 5,568,319 A | 10/1996 | Kaneko et al. |
| 5,569,248 A | 10/1996 | Mathews |
| 5,591,165 A | 1/1997 | Jackson |
| 5,591,167 A | 1/1997 | Laurain et al. |
| 5,601,562 A | 2/1997 | Wolf et al. |
| 5,613,968 A | 3/1997 | Lin |
| 5,613,971 A | 3/1997 | Lower et al. |
| 5,616,142 A | 4/1997 | Yuan et al. |
| 5,616,143 A | 4/1997 | Schlapfer et al. |
| 5,624,442 A | 4/1997 | Mellinger |
| 5,643,273 A | 7/1997 | Clark |
| 5,645,596 A | 7/1997 | Kim et al. |
| 5,672,175 A | 9/1997 | Martin |
| 5,672,176 A | 9/1997 | Biedermann et al. |
| 5,681,319 A * | 10/1997 | Biedermann et al. ........ 606/104 |
| 5,681,320 A | 10/1997 | McGuire |
| 5,683,392 A | 11/1997 | Richelsoph |
| 5,704,937 A | 1/1998 | Martin |
| 5,716,356 A | 2/1998 | Biedermann et al. |
| 5,720,751 A | 2/1998 | Jackson |
| 5,725,532 A | 3/1998 | Shoemaker |
| 5,728,097 A | 3/1998 | Mathews |
| 5,735,857 A | 4/1998 | Lane |
| 5,741,266 A | 4/1998 | Moran et al. |
| 5,752,962 A | 5/1998 | D'Urso |
| 5,766,252 A | 6/1998 | Henry et al. |
| 5,766,253 A | 6/1998 | Brosnahan |
| 5,772,594 A | 6/1998 | Barrick |
| 5,776,199 A | 7/1998 | Michelson |
| 5,782,830 A | 7/1998 | Farris |
| 5,792,044 A | 8/1998 | Foley et al. |
| 5,797,911 A | 8/1998 | Sherman et al. |
| 5,851,183 A | 12/1998 | Bucholz |
| 5,871,445 A | 2/1999 | Bucholz |
| 5,873,878 A | 2/1999 | Harms et al. |
| 5,879,350 A | 3/1999 | Sherman et al. |
| 5,888,224 A | 3/1999 | Beckers et al. |
| 5,888,226 A | 3/1999 | Rogozinski |
| 5,888,227 A | 3/1999 | Cottle |
| 5,891,034 A | 4/1999 | Bucholz |
| 5,891,150 A | 4/1999 | Chan |
| 5,891,158 A | 4/1999 | Manwaring et al. |
| 5,902,231 A | 5/1999 | Foley et al. |
| 5,904,683 A | 5/1999 | Pohndorf et al. |
| RE36,221 E | 6/1999 | Breard et al. |
| 5,910,141 A | 6/1999 | Morrison et al. |
| 5,941,885 A | 8/1999 | Jackson |
| 5,964,761 A | 10/1999 | Kambin |
| 6,033,406 A | 3/2000 | Mathews |
| 6,036,692 A | 3/2000 | Burel et al. |
| D425,989 S | 5/2000 | Michelson |
| 6,080,158 A | 6/2000 | Lin |
| 6,090,113 A | 7/2000 | Le Couedic et al. |
| 6,093,207 A | 7/2000 | Pisharodi |
| 6,099,528 A | 8/2000 | Saurat |
| 6,123,705 A | 9/2000 | Michelson |
| 6,123,707 A | 9/2000 | Wagner |
| 6,139,549 A | 10/2000 | Keller |
| 6,146,386 A | 11/2000 | Blackman et al. |
| 6,149,688 A | 11/2000 | Brosnahan et al. |
| 6,162,223 A | 12/2000 | Orsak et al. |
| 6,179,873 B1 | 1/2001 | Zientek |
| 6,183,477 B1 | 2/2001 | Pepper |
| 6,210,412 B1 | 4/2001 | Michelson |
| 6,226,548 B1 | 5/2001 | Foley et al. |
| 6,235,028 B1 | 5/2001 | Brumfield et al. |
| 6,287,313 B1 | 9/2001 | Sasso |
| 6,302,914 B1 | 10/2001 | Michelson |
| 6,458,159 B1 | 10/2002 | Thalgott |
| 6,485,491 B1 | 11/2002 | Farris et al. |
| 6,530,926 B1 | 3/2003 | Davison |
| 6,530,929 B1 | 3/2003 | Justis et al. |
| 6,562,046 B2 | 5/2003 | Sasso |
| 6,575,899 B1 | 6/2003 | Foley et al. |
| 6,599,294 B2 | 7/2003 | Fuss et al. |
| 6,669,698 B1 | 12/2003 | Tromanhauser et al. |
| 6,793,656 B1 | 9/2004 | Mathews |
| 6,821,277 B2 | 11/2004 | Teitelbaum |
| 6,916,320 B2 | 7/2005 | Michelson |
| 7,008,422 B2 * | 3/2006 | Foley et al. ............. 623/17.16 |
| 7,011,660 B2 | 3/2006 | Sherman et al. |
| 7,060,068 B2 | 6/2006 | Tromanhauser et al. |
| 7,063,725 B2 | 6/2006 | Foley |
| 7,066,961 B2 | 6/2006 | Michelson |
| 7,188,626 B2 * | 3/2007 | Foley et al. ............... 128/898 |
| 7,320,688 B2 | 1/2008 | Foley et al. |
| 7,341,587 B2 | 3/2008 | Molz, IV et al. |
| 7,455,685 B2 | 11/2008 | Justis |
| 7,462,182 B2 | 12/2008 | Lim |
| 7,465,306 B2 | 12/2008 | Pond, Jr. et al. |
| 7,468,064 B2 | 12/2008 | Bruneau et al. |
| 7,473,267 B2 | 1/2009 | Nguyen et al. |
| 2002/0045904 A1 | 4/2002 | Fuss et al. |
| 2002/0087212 A1 | 7/2002 | James et al. |
| 2002/0120334 A1 | 8/2002 | Crozet |
| 2002/0161368 A1 | 10/2002 | Foley et al. |
| 2003/0060826 A1 | 3/2003 | Foley et al. |
| 2003/0208203 A1 | 11/2003 | Lim et al. |
| 2003/0229347 A1 | 12/2003 | Sherman et al. |
| 2005/0021031 A1 | 1/2005 | Foley et al. |
| 2005/0171540 A1 | 8/2005 | Lim et al. |
| 2006/0111714 A1 * | 5/2006 | Foley ....................... 606/61 |
| 2006/0149238 A1 * | 7/2006 | Sherman et al. ............ 606/61 |

| | | | |
|---|---|---|---|
| 2006/0200135 A1* | 9/2006 | Sherman et al. | 606/61 |
| 2006/0229614 A1 | 10/2006 | Foley et al. | |
| 2006/0247630 A1 | 11/2006 | Lott et al. | |
| 2006/0264942 A1 | 11/2006 | Lim et al. | |
| 2007/0049931 A1 | 3/2007 | Justis et al. | |
| 2007/0185491 A1 | 8/2007 | Foley et al. | |
| 2007/0191836 A1 | 8/2007 | Justis | |
| 2007/0198015 A1* | 8/2007 | Foley et al. | 606/61 |
| 2007/0213714 A1 | 9/2007 | Justis | |
| 2008/0249531 A1 | 10/2008 | Patterson | |
| 2008/0319477 A1 | 12/2008 | Justis et al. | |

FOREIGN PATENT DOCUMENTS

| | | |
|---|---|---|
| DE | 196 26 754 A1 | 1/1998 |
| DE | 100 27 988 A1 | 1/2002 |
| EP | 260044 | 3/1988 |
| EP | 0 528 562 A2 | 2/1993 |
| EP | 0528177 | 2/1993 |
| EP | 1099429 | 5/2001 |
| EP | 1201207 | 5/2002 |
| FR | 2736538 | 1/1997 |
| SU | 0839513 A | 6/1981 |
| WO | WO 97/30666 | 8/1997 |
| WO | WO 97/38639 | 10/1997 |
| WO | WO 99/15097 | 4/1999 |
| WO | WO 99/26549 | 6/1999 |
| WO | WO 00/44288 | 8/2000 |
| WO | WO 01/28436 | 4/2001 |

OTHER PUBLICATIONS

Sofamor Danek, The Spine Specialist; Horizon Spinal System, Surgical Technique; as described by Samuel J. Laufer, MD, J. Andrew Bowe, MD, Copyright 1999.
Posterior Percutaneous Spine Instrumentation; 9 (Suppl 1) Eur Spine J (2000) Received: Sep. 3, 1999, Accepted: Sep. 4, 1999.
Synthes Spine, "Universal Spinal Systems (USS) Technique Guide", Jun. 1997.
Synthes Spine, "Cervical Spine Locking Plate System", Synthes 1995 Product Catalog, 1995.
Acromed, "AcroPlate—Anterior Cervical System", AcroMed 1994 Product Catalog, 1994.
Depuy, "Anterior Product Compression Catalog Plate", DePuy 1996 Product Catalog, 1996.
Callahan, J. et al., "Percutaneous Lumbar Discectomy: A New Adjunct Open Surgery" Indiana Medicine, 84(3), pp. 188-190, Mar. 1991.
Daniaux, H., et al. "Application of Posterior Plating and Modifications in Thoracolumbar Spine Injuries," Spine, 16 (Supp.3), pp. S127-S132, 1991.
De Oliveira, J.C. "Anterior Plate Fixation of Traumatic Lesions of the Lower Cervical Spine," Spine, 12(4), 1987.
Kambin, P. "Posterolateral Percutaneous Lumbar Discectomy and Decompression: Arthroscopic Microdiscectomy," Arthroscopic Microdiscectomy, Ch. 6, 1991.
Hijikata, S., "Percutaneous Nucleotomy, A new Concept Techniques and 12 Years' Experience," Clinical Orthopaedics and Related Research, 238, Jan. 1989.
Mathews, H.H., et al. Laparoscopic Discectomy with Anterior Lumbar Interbody Fusion, Spine 20(16), pp. 1797-1802, 1995.
Mathews, H.H. "Percutaneous Interbody Fusions," Orthopedic Clinics of North America, vol. 29, No. 4, Oct. 1998.
Moran, J.M., et al., "Transpedicular Screw Fixation," Journal Orthopaedic Research, vol. 7 pp. 107-114, 1989.
Schreiber, A., et al., "Does Percutaneous Nucleotomy With Discoscopy Replace Conventional Discectomy?" Clincial Orthopaedics and Related Research, No. 238, Jan. 1989.
Suezaway, Y. et al., "Percutaneous Nucleotomy An Alternative to Spinal Surgery," Archives of Orthopaedic and Traumatic Surgery, No. 105, pp. 287-295, 1986.
Zindrick, M.R., "The Role of Transpedicular Fixation Systems for Stablization of the Lumbar Spine," Orthopaedic Clinics of North America, vol. 22, No. 2, Apr. 1991.

Kambin, P., "Arthoscopic Fusion of the Lumbosacral Spine," Lumbosacral and Spinopelvic Fixation, 1996.
Schreiber, A., et al., "Percutaneous Nucleotomy: Technique with Discoscopy", Orthopedics, vol. 14, No. 4, Apr. 1991.
Harrington, P., "Treatment of Scoliosis: Correction and Internal Fixation by Spine Instrumentation", Journal of Bone and Joint Surgery Am, 44:591-634, 1962.
Gillespie, R., et al., "Harrington Instrumentation Without Fusion", Journal of Bone and Joint Surgery, 1981; 63-B(3), 461, 1981.
Patterson, J.F., et al., "The Operative Treatment of Progressive Early Onset Scoliosis: A Preliminary Report", Spine, 15(8), 809-815, 1990.
Vanlommel, E. et al., "Harrington Instrumentation Without Fusion for the Treatment of Scoliosis in Young Children", Journal of Pediatric Orthopaedics Part B, 1.116-8, 1992.
Tello, C.A., "Harrington Instrumentation Without Arthrodesis and Consecutive Distraction Program for Young Children with Severe Spinal Deformities: Experience and Technical Details", Orthopaedic Clinics of North America, 25 (2), 333-351, 1994.
Klemme, W.R. et al., "Spinal Instrumentation Without Fusion for Progressive Scoliosis in Young Children," Journal of Pediatric Orthopaedics, 17,734-42,1997.
Mineiro, J. et al., "Subcutaneous Rodding for Progressive Spinal Curvatures: Early Results", Journal of Pediatric Orthopaedics, 22, 290-5, 2002.
Moe et al., "Harrington Instrumentation Without Fusion Plus External Orthotic Support for the Treatment of Difficult Curvature Problems in Young Children", Clinical Orthopaedics and Related Research, 185, 35-45, 1984.
Globus Medical, "Pivot System", Minimally Invasive Products, Copyright 2005 Globus Medical, wwvv. globusmedical.com.
Aebi, M. et al., AO ASIF Principles in Spine Surgery, pp. 119-120, Dec. 23, 1997.
Synthes Spine, "The Universal Spinal System: Surgical Technique Guide for the Correction of Scoliosis", 1994.
Cunningham, B.W. et al., "Video-Assisted Thoracoscopic Surgery Versus Open Thoracotomy for Anterior Thoracic Spinal Fusion," Spine, 23( 12), Jun. 1998.
Fedder, I.L. et al., "Video-Assisted Spinal Surgery: Laboratory Protoco!," in, Atlas of Endoscopic Spine Surgery, Regan, J.F., et al., Eds., Quality Medical Publishing, Inc.
Rosenthal, D. et al., "Newer Applications of Spinal Instrumentation," in, Atlas of Endoscopic Spine Surgery, Regan, J.F.et al., Eds., Quality Medical Publishing, Inc., St. Louis, pp. 333-337, 1995.
Avallone, Eugene A. et al., Marks' Standard Handbook for Mechanical Engineers, 10th Ed., p. 8-3,1996.
Phelan, RM., Fundamentals of Mechanical Design, 3rd Ed., pp. 6-7, 72, 1957.
Rothbart, H.A., CAMS Design, Dynamics, and Accuracy, p. 4, 1956.
Globus Medical, "Suslain-O—Radiolucent Space System", Globus Medical Copyright 2006, www,globusmedical com.
Globus Medical, "Pivot Minimally Stabilization System Surgical Technique", Globus Medical, (date unknown).
Perez-Cruet, M, J. et al., eds "An Anatomic Approach To Minimally Invasive Spinal Surgery", Ch. 33 (Quality D Medical Publishing), 2006.
Wang, M. Y. et al., "Minimally Invasive Posterior Lumbar Fusion Techniques", Elsevier, 2005.
Lippincott, Williams, & Wilkins, Stedman's Medical Dictionary, 27 Ed., "percutaneous", p. 1345, 2000.
Obray, R.W., "MR Imaging and and Osseous Spinal Intervention and Intervertebral Disk Intervention", Magnetic Resonance Imaging Clinics, Elsevier, 2007.
Rodts, G., "New Technology Advances Minimally Invasive Spine Surgery", Spine Universe, www,spineuniverse,com,' printed on Oct. 10, 2007.
Healthwise, "Percutaneous Disectomy for Herniated Disc", BC Health Guide, www.healthwise,org, printed Oct. 10, 2007.
Heini, Paul F. et al., "The Use of a Side-Opening Injection Cannula in Vertebroplasty", Spine, 27(1), 2002.
Skinner, Harry B, Ed., Current Diagnosis &Treatment in Orthopedics (2nd edition), p. 198, 2003.
Globus Medical, "Excellence in Spine" Brochure, (date unknown).

Ditsworth, D., "Comprehensive Percutaneous Endoscopic Spinal Surgery" AANS 1995 Annual Meeting, Abstract, Apr. 1995.
Globus Medical, "Global Medical Launches Sustain 0", Press Release, wvwv.globusmedical.com, Aug. 10, 2006.
Bohlman, H.H. et al., "Spinal Cord Monitoring of Experimental Incomplete Cervical Spinal Cord Injury", Spine, vol. 6, No. 5, Sep./Oct. 1981.
Regan. J. et al., "Endoscopic Techniques in Spinal Surgery", Clinical Orthopaedics and Related Research, No. 335, pp. 122-139, Feb. 1997.
Maciejczak et al., "Posterior Keyhole Corpectomy with Percutaneous Pedicle Screw Stabilization in the Surgical Management of Lumbar Burst Fractures". Operative Neurosurgery 2, vol. 60, Apr. 2007.
Aunqble et al., "Video-assisted AUF with Cage and Anterior Plate Fixation for L5-S1 Spondylolisthesis", J. of Spinal Discord Tech., vol. 19. No. 7, Oct. 2006.
Sahin et al., "Minimally Incisional Stabilization of Unstable L5 Burst Fracture", J of Spinal Discord Tech, vol. 18, No. 5, Oct. 2005.
NEWSRX. "Transforminal Lumbar Interbody Fusion with Minimal Access Study Released", May 30, 2005.
Wang et ai "Minimally Invasive Posterior Lumbar Fusion Techniques." Operative Techniques in Neurosurgery, Elsevier, 2005.
MEDSTAR.COM, "Sextant Spinal Surgery", www.News14.com. Mar. 11, 2004.
Medical Industry Week, "Medtronic Introduces New Technique for Minimally-Invasive Spinal Surgery", Medtronic, Oct. 22, 2003.
Acosta et ai, "Use of Intraoperative Isocentric C-arm 3D Fluoroscopy for Sextant Percutaneous Pedicle Screw Placement: Case Report and Review of the Literature", The Spine Jou.
Beringer et al., "Unilateral Pedicle Screw Instrumentation for Minimally Invasice Transformational Lumbar Interbody Fusion", Neurosurg Focus 20, (3):E4, 2006.
Rodts, G., "Percutaneous Lumbar Pedicle Screws: Indications, Technique, Results", Haio et ai, eds, Advances in Spinal Stabilization, Prog, Neurol Surg., Basel, Karger, 2003, vol. 16, pp. 204-212.
Khoo et ai, "Minimally Invasive Percutaneous Posterior Lumbar Interbody Fusion", Neurosurgery, vol. 51, Supplement 2, Nov. 2002.
Neurological Surgery, "Reid Introduces New Spine Surgery to the Region", www.tnbrainandspine.com. Oct. 19, 2005.
Manning, A., "No Pain, All Gain" Tennessee Alumnus Magazine, vol. 86, No. 1, Winter, 2006.
Bindal et al., "Intraoperative Electromyography Monitoring in Minimally Invasice Transforminal Lumbar Interbody Fusion", J. Neurosurg. Spine, vol. 6, pp. 126-132, 2007.
Sells, T., "Finalists Named for Annual Health Care Heroes." Memphis Business Journal, Jul. 27, 2007.
Powers, et ai, "Placement of Percutaneous Pedicle Screws without Imaging Guidance", Neurosurg. Focus 20(3):E3, Mar. 2006.
Mummaneni et al., "The Mini-Open Transforminal Lumbar Interbody Fusion", Operative Neurosurgery 4, vol. 57, Oct. 2005.

Schwender et al., "Minimally Invasive Transforminal Lumbar Interbody Fusion (TUF)", J, Spinal Discord Tech, vol. 18, Supplement 1, Feb. 2005.
German et al., "Minimal Access Surgical Techniques in the Management of Painful Lumbar Motion Segment", Spine, vol. 30, No. 165, pp. 552-559, 2005.
Foley et al., "Minimally Invasive Lumbar Fusion", Spine, vol. 28, No. 155, pp. 526-535, 2003.
Park et al., "Percutaneous Pedicle Screw Fixation of the Lumbar Spine", Orthopaedic Surgery Spine, European Musculoskeletal Review 2002.
Mayer, "Memphis Neurosurgeon's Capstone Implant Providing Hope for Patients", Memphis Medical News, Copyright 2007.
Childers, "New Device May Be Able to Rebuild Spine: Video Mary Ann Childers reports", Chicago, CBS-2, May 30, 2005, www.cbs2chicago.com.
Cloward, "Acute Cervical Spine Injuries", Clinical Symposia, vol. 32, No. 1,1980.
Assaker, "Minimal Access Spinal Technologies: State-of-the-art, Indications, and Technologies", Joint Bone Spine, 71, pp. 459-469, 2004.
Criscitiello et al., "Principles of Endoscopic Techniques to the Thoracic and Lumbar Spine", Chapter 15, pp. 153-158, (date unknown).
McAfee et al., "Anterior Thoracic Corpectomy for Spinal Cord Decompression Performed Endoscopically", Surgical Laparoscopy and Endoscopy, vol. 5, No. 5, pp. 339-348, 1995.
McAfee et al., "The Incidence of Complications in Endoscopic Anterior Thoracolumbar Spinal Reconstructive Surgery", Spine, vol. 20, No. 14, pp. 1624-1632, 1995.
Zucherman et al., "Instrumented Laparoscopic Spinal Fusion: Preliminary Results", Spine, vol. 20, No. 18, pp. 2029-2035, 1995.
Mahvi et al., "A Prospective Study of Laparoscopic Spinal Fusion", Annals of Surgery, vol. 224, No. 1, pp. 85-90, 1996.
Buhren et al., "Minimal-Invasive ventrale Spondylodesen bei Verletzungen der Brust-und lendenwirbelsaule 35 (Minimally Invasive Ventral Spondylodesis for Injuries of the Thoraric and Lumbar Spine)", Der Chirurg, 68, pp. 1076-1084, 1997.
Reexamination Ctrl. No. 90/009,272—Response to Office Action Dated Oct. 20, 2009, including Exhibit B., Declaration of Scott G. Tromanhauser, M.D., M.B.A. dated Oct. 16, 2009.
Reexamination Ctrl. No. 90/009,273—Resp. To Office Action dated Nov. 3, 2009, including Ex. A., Interrogs. to the Jury for the 6,530,929 and 7,008,422 Patents, Ex. B., Memorandum and Order dated Mar. 18, 2008, and Ex. C., Decl. Of Scott G. Tromanhauser, M.D., M.B.A. dated Nov. 1, 2009.
Reexamination Ctrl. No. 90/009,277—Response to Office Action dated Nov. 16, 2009, including Exhibit A., Declaration of Scott G. Tromanhauser, M.D., M.B.A. dated Nov. 14, 2009.

* cited by examiner

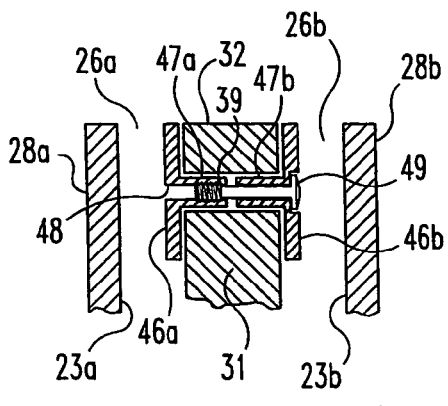
*Fig. 2*
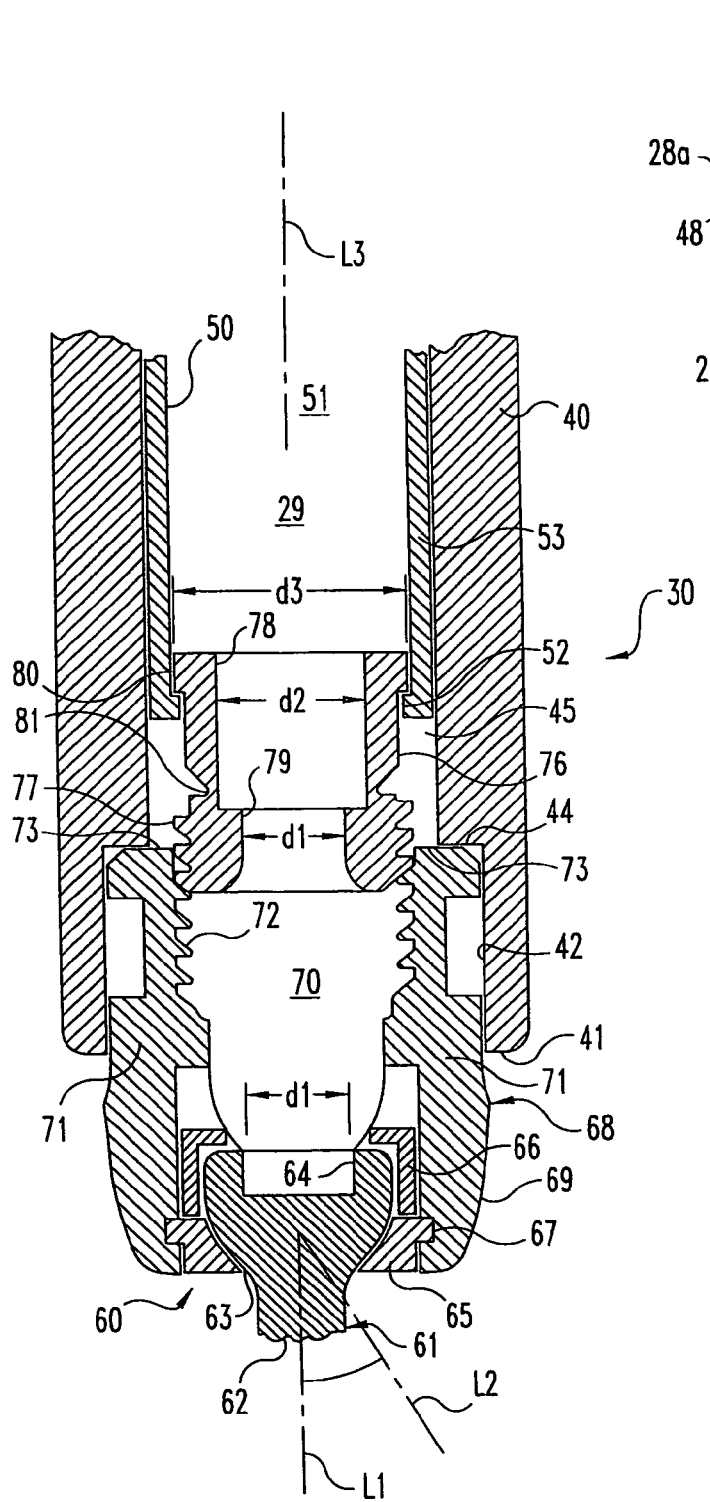
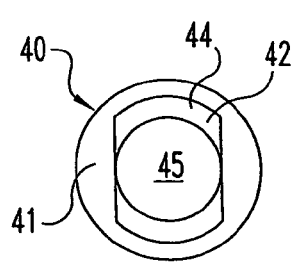
*Fig. 5*
*Fig. 4*

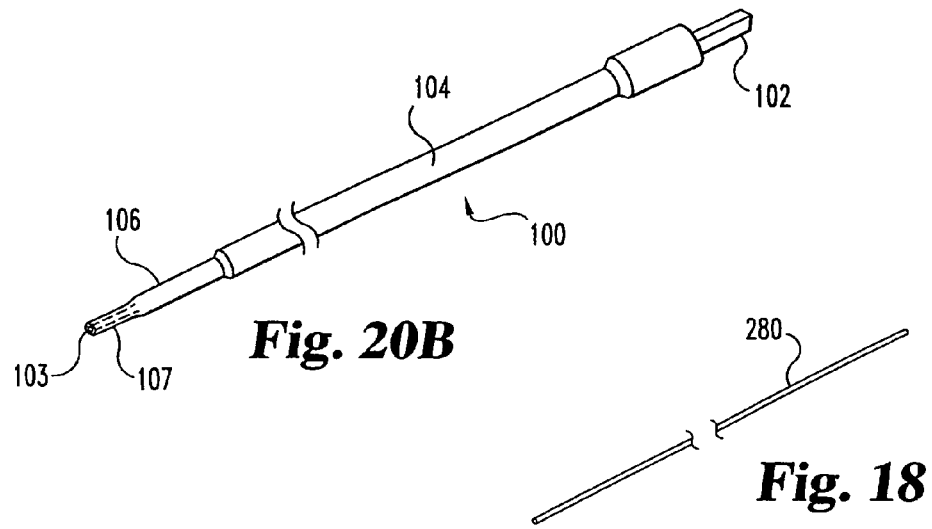
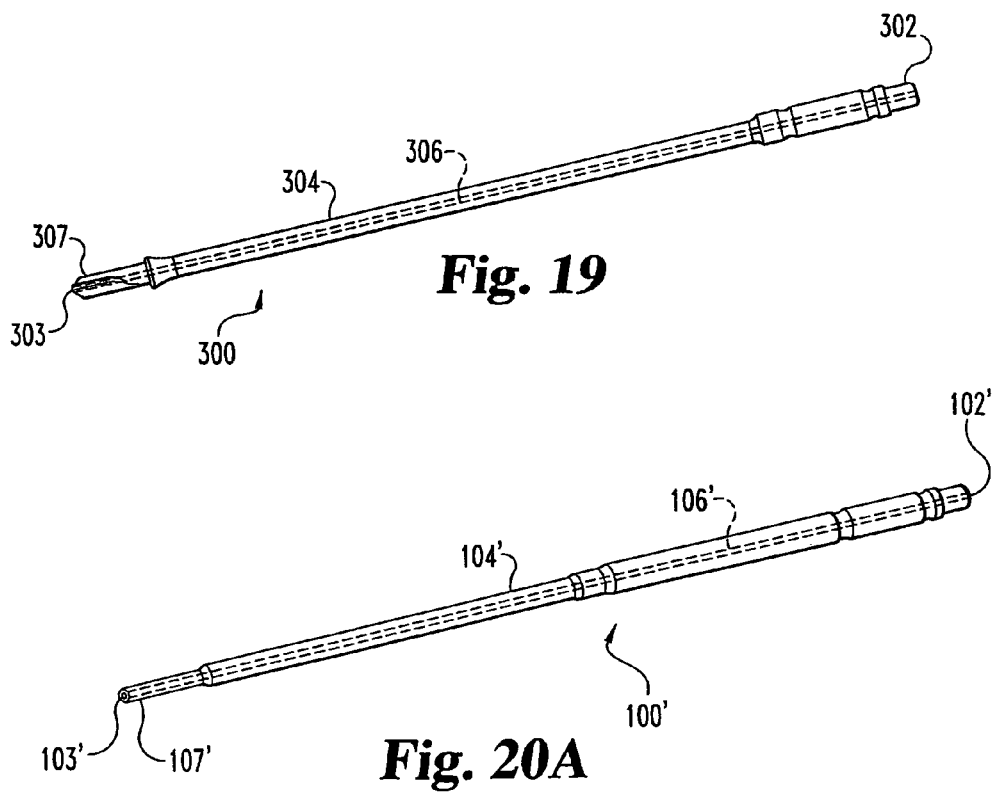

INSTRUMENTS AND METHODS FOR STABILIZATION OF BONY STRUCTURES

CROSS-REFERENCE TO RELATED APPLICATIONS

The present application is a divisional of U.S. patent application Ser. No. 10/126,237 filed on Apr. 19, 2002, now U.S. Pat. No. 7,188,626, which is a continuation-in-part of U.S. patent application Ser. No. 09/616,581 filed on Jul. 14, 2000, now issued as U.S. Pat. No. 6,530,929, which claims the benefit of the filing dates of Provisional Application Ser. No. 60/186,729, filed Mar. 3, 2000 and Provisional Application Ser. No. 60/160,489, filed Oct. 20, 1999. The referenced applications are each incorporated herein by reference in their entirety.

BACKGROUND

The present invention generally relates to surgical instruments and methods for use of the same, and more particularly, but not exclusively, relates to instruments and methods for stabilizing bony structures.

The use of various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations deep within the body and the danger of damage to vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption.

Examples of instruments and techniques for performing surgeries using minimally invasive techniques are found in U.S. Pat. Nos. 5,792,044 and 5,902,231 to Foley et al. While these techniques are steps in the right direction, there remains a need for instruments and methods for stabilizing bony structures using minimally invasive techniques. This need and others are addressed by the present invention.

SUMMARY

The present invention relates to devices and methods for insertion of an orthopedic brace or connecting element to one or more anchors secured to an animal subject.

In one aspect of the invention, there is provided a method for using an instrument to connect at least two bone anchors with a connecting element. The instrument is secured to one or both the anchors and manipulated to place the connecting element in a position more proximate at least one of the anchors.

In another aspect of the present invention, there is provided a method that includes: placing at least two anchors in a bony structure, each of the anchors having an extension associated therewith; attaching a brace inserter of an installation instrument to the extensions; and guiding a brace into a desired position relative to the anchors.

In a further aspect of the invention, there is provided an instrument for placing a brace or connecting element into a desired position relative to at least two anchors. The instrument employs a fixed geometric relationship to guide the connecting element into a position proximate the anchors.

In yet a further aspect of the invention, there is provided an instrument for placing a connecting element into a desired position proximate the location of two anchors. The instrument is mounted to the at least two anchors and holds the connecting element in spatial relation to the anchors about a pivot point. The instrument is rotated about the pivot point to guide the connecting element to the desired position.

According to an additional aspect of the invention, there is provided an installation instrument having a brace secured thereto. The brace is indexed so that the brace can assume only a desired orientation when secured to the installation instrument.

According to one aspect of the invention, the percutaneous brace placement device includes first and second anchor extensions and a pivoting brace inserter mounted to the anchor extensions about a pivot axis. The pivoting brace inserter includes an arm having a brace mounting portion at its distal end for connecting an orthopedic brace to the device.

In another aspect of the present invention, the installation instrument includes a support arm engaged to the anchor extension. An anchor is engaged to the distal end of each anchor extension. Preferably, the anchors are in the form of a multi-axial screw capable of allowing universal rotation of the anchor extension. In one form, the arm is located at a predetermined radius from the pivot axis and in a curve at a substantially constant radius relative to the pivot axis to the brace mounting portion. In yet another form, a brace gripper or coupler is operable to selectively grip and release an orthopedic brace from the inserter. In another form, a brace has one end connected at the brace mounting portion and an opposite end adapted to puncture soft tissue of an animal body. Preferably, the brace and pivot arm lie in a circle centered on the pivot axis at a constant radius. The brace is curved at the constant radius relative to the pivot axis in one plane, and the brace is oriented to lie in the circle.

According to another aspect of the invention, a method of installing an orthopedic brace in an animal subject is provided. The method comprises placing first and second anchors mounted on first and second anchor extensions, respectively, percutaneously in first and second bony parts of the body of the subject; mounting a brace inserter on the anchor extensions, the inserter having a pivot axis about the anchor extensions; mounting the brace on the pivoting brace inserter; and swinging the brace inserter relative to the anchor extensions about the pivot axis and thereby moving the brace in a forward direction through an arc centered on the pivot axis and introducing an end of the brace percutaneously to the location of the anchors. In a further form, the brace is fixed to the anchors; the inserter disconnected from the brace; and the inserter moved in a reverse direction through the arc and to remove the inserter from the body. Preferably, the brace is a shaft curved at a single radius about an axis co-linear with the pivot axis of the arc, and the method further includes introducing the shaft through receivers in the anchors during the introduction step.

In yet another aspect of the present invention, anchors, or anchors and anchor extensions are placed by image guided navigation to locate optimum placement and orientation of the anchors in pedicles of vertebral bodies of a single level of the spine of the animal. The image guided technology is also used to determine animal skin locations for percutaneous puncture entry of the anchors. In one form the anchors are cannulated and inserted over guidewires anchored in the vertebral bodies.

According to another aspect of the invention, a technique for spinal fusion of adjacent vertebral bodies of the animal spine is provided. The method includes removal of intervertebral disc material from the space between first and second vertebral bodies of the subject. One or more interbody fusion devices are introduced into the space. First and second anchors are engaged to the first and second vertebral bodies, respectively, through first and second percutaneous punctures in the subject. A curved brace is installed through a third percutaneous puncture in the subject using an installation instrument. The brace is connected to the anchors by application of fastening tool to the anchors through the first and second punctures.

In another form of the present invention, a curved brace is installed by swinging the brace through an arc in a plane containing the brace and perpendicular to the axis of curvature of the brace, and passing portions of the brace into passageways in the anchors. The pivot axis of the brace is at a fixed distance from the passageways equal to the radius of curvature of the brace.

Techniques for minimally invasive surgery are provided in which first and second anchors are inserted through a single incision and engaged to respective ones of first and second vertebrae. A connecting element is positioned proximate the first and second anchors from an entry location into the patient remote from the incision.

One object of the present invention of the present invention is to provide minimally invasive techniques and instruments for stabilizing a bony structure in an animal subject.

Related features, aspects, embodiments, objects and advantages of the present invention will be apparent from the following description.

BRIEF DESCRIPTION OF THE DRAWINGS

FIG. 2 is an enlarged fragmentary section view taken at line 2-2 of FIG. 1 and viewed in the direction of the arrows.

FIG. 3 is an enlarged fragmentary exploded view of the connection of the brace to a portion of the installation instrument.

FIG. 4 is an enlarged section view of a portion of the installation instrument taken at line 4-4 of FIG. 1.

FIG. 5 is an end view, on a smaller scale than FIG. 4, of an outer sleeve comprising a portion of the installation instrument of FIG. 1.

FIG. 18 is a perspective view of a guidewire.

FIG. 19 is a perspective view of a cannulated awl usable in a surgical technique with the installation instrument of the present invention.

FIGS. 20a and 20b are perspective views of driver tools usable in a surgical technique with the installation instrument of the present invention.

DESCRIPTION OF THE ILLUSTRATED EMBODIMENTS

Figure 1:
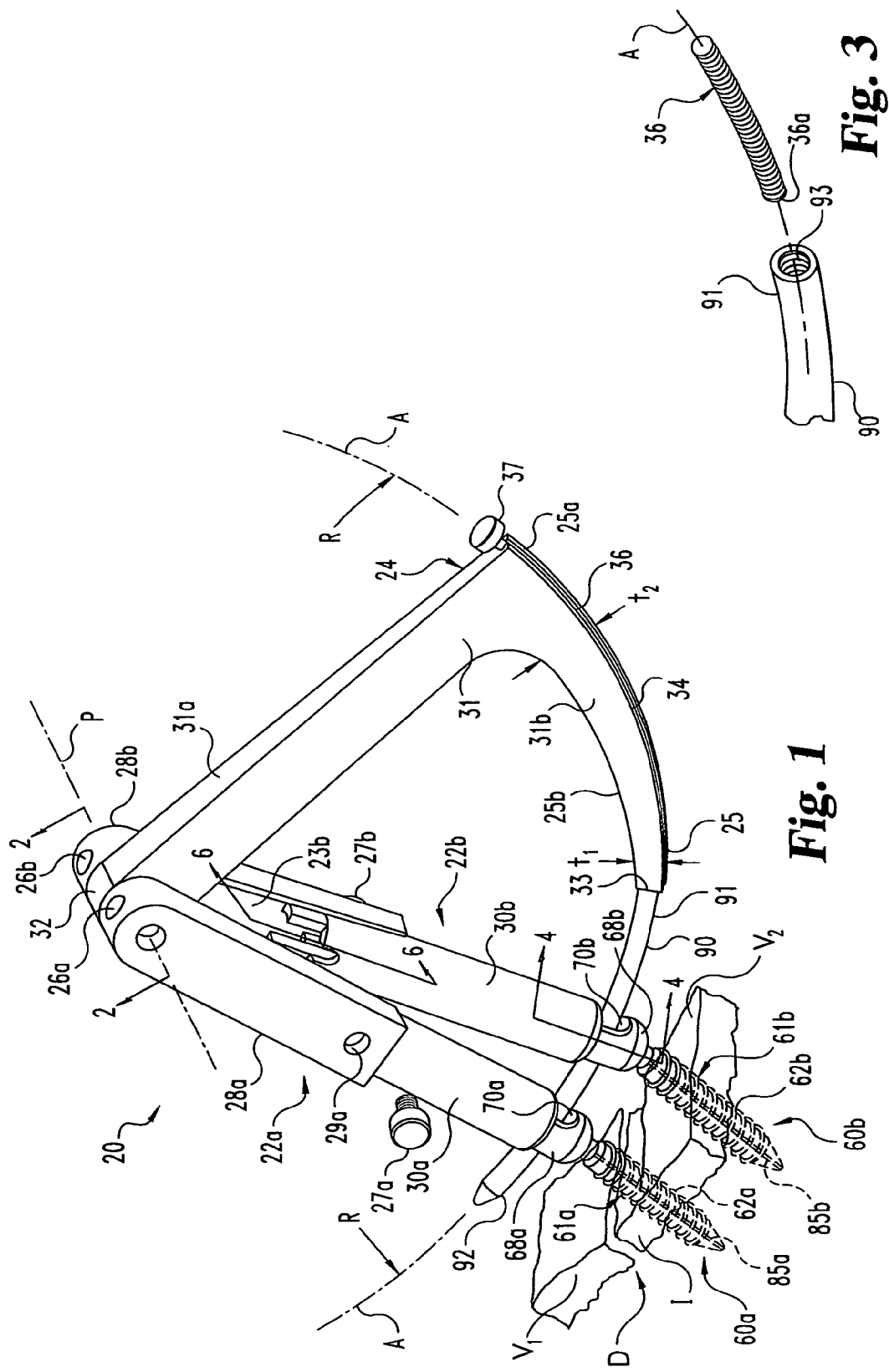
FIG. 1 is a perspective view of a brace and an installation instrument for installing the brace according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

The present invention is directed to instruments and methods for insertion of a brace for connection with anchors engaged to bony parts of the body. Referring to FIG. 1, connecting element or brace 90 is preferably an elongated rod or shaft curved along its length between a connecting end 91 and an insertion end 92 with a radius of curvature R. However, it should be understood that the present invention contemplates that brace 90 can include any configuration known for a rod, implant, or fastener, so long as brace 90 is insertable using installation instrument 20. Further, brace 90 can be elastic or super-elastic member in the form of a cable, band or artificial ligament that used in tethering or other surgical procedures. Non-rigid bracing elements can be positioned with respect to the anchors with a rigid guide member therealong or at the leading end thereof, which can be thereafter removed once the non-rigid bracing element is in its desired position or left in the patient's body. Brace 90 can be percutaneously or non-percutaneously inserted with an installation instrument 20 into passageways of anchors engaged to a bony structure in the body of an animal subject to stabilize the bony structure.

In the illustrated embodiment, brace 90 is a shaft curved at a single radius R along an arc A, and brace 90 has an axis co-linear with arc A. However, it is contemplated that brace 90 can have a curvature that differs from arc A, or can have a curvature that varies or is compounded along its length. The curvature of brace 90 can be defined by any one or any combination of mathematical relationships, including, for example, linear, exponential, logarithmic, trigonometric, geometric, parabolic, quadratic, cubic, hyperbolic, elliptic, or parametric relationships. Brace 90 in FIG. 1 is inserted via the installation instruments of the present invention through passageways 70a and 70b of anchors 60a and 60b, respectively in order to stabilize adjacent vertebrae V1 and V2. The installation instrument can employ any type of fixed geometric relationship to insert brace 90 into passageways 70a and 70b. This fixed geometric relationship can be governed by any one or combination of a pinned joint, a cam, a four-bar linkage, a guide member that provides a path for translational movement of brace 90, or any other mechanical relationship that would occur to those skilled in the art.

Installation instrument 20 illustrated in FIG. 1 includes a first support arm 22a and a second support arm 22b. Support arms 22a, 22b are pivotally connected at a proximal end 32 of a brace inserter 24. Brace inserter 24 includes a distal end 33 from which a brace 90 extends. A pivot arm 31 has a straight portion 31a extending from proximal end 32 to a curved portion 31b that extends to a brace mounting portion 25 at distal end 33. Inserter 24 is pivotable about a pivot axis P to define a curvilinear arc or axis A. Brace mounting portion 25 includes a brace receiving opening 35 at distal end 33.

Figure 3A:
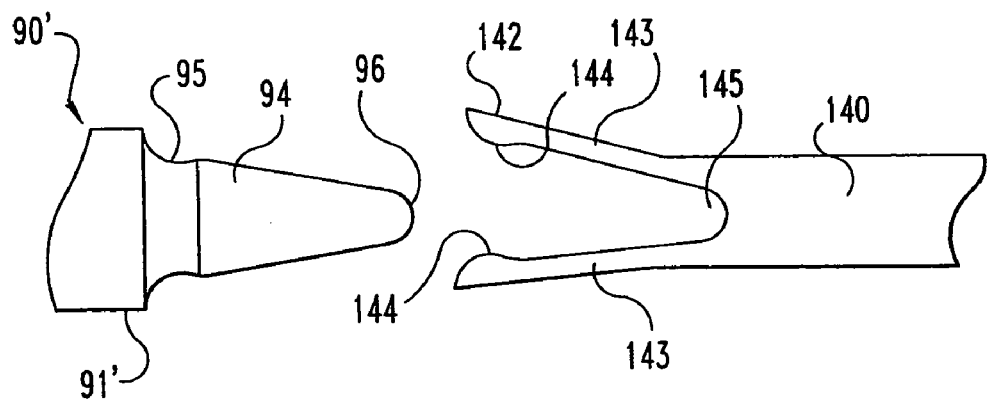
FIG. 3a is an enlarged fragmentary exploded view of another embodiment connection of the brace to a portion of the installation instrument.

Preferably, brace 90 is supported by mounting portion 25 in receiving opening 35 so that brace 90 is relatively fixed with respect to inserter 24, maintaining alignment of brace 90 along arc axis A during insertion of brace 90. Curved portion 31b includes a channel 34 extending therealong that receives a brace coupler 36 therein. Preferably, brace coupler 36 is an elongated pin that extends along arc axis A from distal end 33 to a thumb screw 37 adjacent pivot arm 31. As shown in FIG. 3, brace coupler includes an elongated pin having a distal end 36a that is preferably threaded, and is received within an internally threaded bore 93 formed at brace connecting end 91. It is further contemplated that the pin can be a wire or a flexible rod. Thumb screw 37 is manipulated by the surgeon to connect brace 90 to inserter 24 at brace mounting portion 25. After brace 90 is inserted, the surgeon manipulates thumbscrew 37 to disconnect brace 90 from inserter 24.

The present invention also contemplates other mechanisms for connecting brace 90 to inserter 24. For example, in FIG. 3a brace coupler 36 includes a draw bar 140 positionable within channel 34. Bar 140 has a distal end 142 with a pair of opposed jaws 143 forming a mouth 145. Each jaw 143 includes a tooth 144 projecting therefrom towards the opposing jaw. Brace 90' is the same as brace 90, except brace 90' has a connecting end 91' with a connecting post 94 extending therefrom.

Connecting post 94 is tapered from connecting end 91' to tip 96, and is configured to mate with jaws 143 in mouth 145 when jaws 143 are clamped around connecting post 94. Connecting post 94 includes a recess 95 formed adjacent connecting end 91' configured to receive teeth 144 therein. In order to clamp connecting post 94, a proximal end of draw bar 140 extends from inserter 24, as shown in FIG. 1 with respect to coupler 36, and has a threaded thumbscrew engaged thereto. The jaws are actuated and clamped around connecting post 94 by threading the thumbscrew in an appropriate direction to draw bar 140 into channel 34. Jaws 143 are pressed towards one another and teeth 144 are received into recess 95, thereby connecting brace 90' to inserter 24. Preferably, connecting post 94 is indexed so that brace 90' can only be coupled to inserter 24 with brace 90' extending along axis A. This indexing can be accomplished by providing two recesses 95 each sized to receive tooth 144 and positioned on post 94 such that brace 90' can only be coupled via teeth 144 if brace 90' is oriented along axis A.

Inserter 24 has a bottom surface 25a that is preferably curved along axis A to facilitate smooth percutaneous insertion of brace 90. Further, curved portion 31b has at mounting portion 25a thickness t1 between bottom surface 25a and a top surface 25b. The thickness increases along the length of curved portion 31b of pivot arm 31 in a smooth taper to a thickness t2 adjacent the straight portion 31a. Thickness t2 is preferably greater than thickness t1, facilitating percutaneous insertion and withdrawal of curved portion 31b while minimizing damage and trauma to the surrounding tissue.

Support arms 22a and 22b have proximal end portions adjacent axis P with tool bores 26a and 26b, respectively, for receiving a driving tool therethrough to manipulate anchors 60a and 60b, respectively, as described further below. In the illustrated embodiment, support arm 22a includes an upper post 28a having a channel 23a extending upwardly to the proximal end portion and communicating with tool bore 26a. An anchor extension 30a is mounted in channel 23a via a thumbscrew 27a threadedly received in a threaded aperture 29a that extends through upper post 28a and anchor extension 30a. Anchor extension 30a is mounted at its lower or distal end to anchor 60a. Similarly, support arm 22b includes an upper post 28b having a channel 23b communicating with tool bore 26b. An anchor extension 30b is mounted in channel 29b via a thumbscrew 27b threadedly received in a threaded aperture (not shown) extending through upper post 28b and anchor extension 30b. Anchor 30b is mounted at its lower or distal end to anchor 60b. The present invention also contemplates that upper post 28a and anchor extension 30a, and similarly upper post 28b and anchor extension 30b, are not separate components but rather are formed as a unit to which brace inserter 24 is pivotably attached.

Inserter 24 is pivotally connected to upper posts 28a and 28b of support arms 22a and 22b, respectively. As shown in FIG. 2, a cross-section taken at line 2-2, inserter 24 is positioned between support arms 22a and 22b. Upper post 28a has a cylindrical portion 46a with a first flanged bushing 47a extending therefrom. Upper post 28b has a cylindrical portion 46b with a second flanged bushing 47b extending therefrom. Bushings 47a and 47b are rotatably received in a through-hole 39 that extends through pivot arm 31. Bushings 47a and 47b define a through opening 48 for receiving a pin 49 therein to secure posts 28a and 28b to pivot arm 31. Preferably, pin 49 is threaded along a portion of its length to engage internal threads in bushing 47a, and the head of pin 49 sits within a countersink formed in cylindrical portion 46b at bushing 47b to maintain clearance of bore 26b.

Figure 2A:
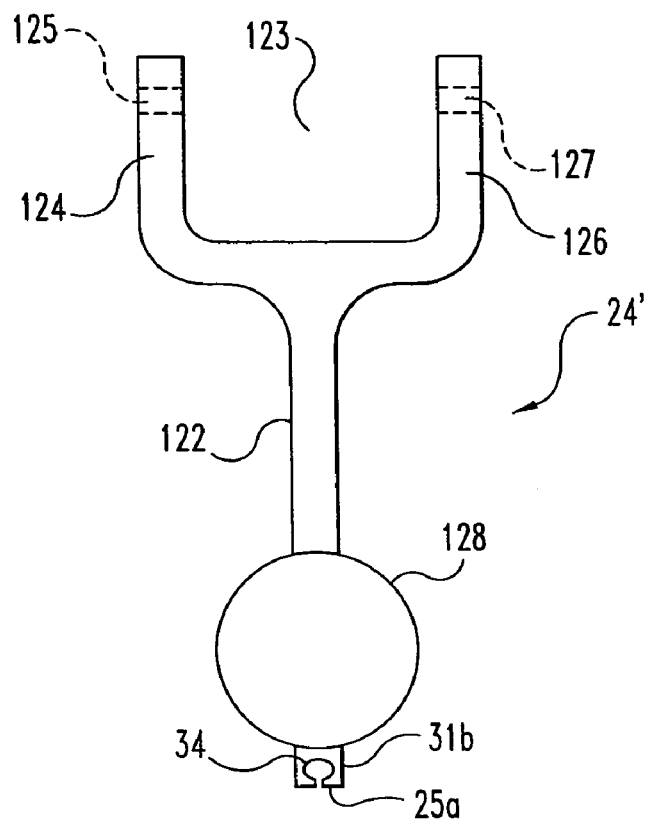
FIG. 2a is a side elevational view of another embodiment of a brace inserter.

An alternate form of pivot arm 31 for pivoting rod inserter 24 is illustrated in FIG. 2a and designated as rod inserter 24', and like elements between inserter 24 and 24' are designated with like reference numerals. Inserter 24' has pivot arm 122 extending from curved portion 31b to a proximal end 123. A handle 128 is positioned adjacent brace mounting portion 25 on pivot arm 122 to facilitate percutaneous insertion of brace 90 and withdrawal of the instrument by the surgeon. A pair of arms 124, 126 adjacent proximal end 123 form a passage therebetween. The passage is configured to receive support arms 22a, 22b between arms 124 and 126. Holes 125 and 127 formed through arm 124 and 126, respectively, are provided for a connection mechanism to pivotally connect inserter 24' to support arms 22a and 22b.

Referring now to FIG. 4, details of anchor extensions 30a and 30b and anchors 60a and 60b (hereinafter collectively referred to as anchor extension 30 and anchor 60) will now be described. In FIG. 4, anchor 60 is shown fragmentarily as a bone screw 61 with its head 63 mounted in a receiver or connector. In FIG. 1, screws 61a and 61b are shown cannulated with central passage 85a and 85b, respectively; however, non-cannulated screws 61 are also contemplated.

In the illustrated embodiment, the receiver or connector is a yoke 68 that defines a passageway 70 for receiving brace 90 therethrough and a set screw 76 to secure brace 90 in yoke 68. Yoke 68 is mountable to anchor extension 30 before and during percutaneous placement and securement of anchor 60 to the bony structure. Anchor extension 30 includes an outer sleeve 40 and an inner sleeve 50 disposed within a bore 45 through outer sleeve 40. Inner sleeve 50 defines a bore 51 therethrough that communicates with the channel and tool bore 26 of the upper post 28 to which inner sleeve 50 is attached (FIG. 1). Distal end 53 of inner sleeve 50 includes a lip 52 extending radially therearound projecting into inner bore 51. Lip 52 retains set screw 76 on inner sleeve 50 with screw 76 at least partially threaded into yoke 68, thereby mounting anchor 60 on anchor extension 30.

Screw 61 has bone engaging threads formed on shank 62 and a head 63 that includes tool opening 64, such as a hex opening or the like, configured to receive a driving tool. In a preferred form, anchor 60 is a multi-axial screw assembly that has yoke 68 pivotably coupled to head 63 of screw 61. However, the use of an anchor 60 that does not include a screw having multi-axial capabilities is not precluded by the present invention. As is known in the art, screw 61 is capable of being rotated within yoke 68 to assume a plurality of angles between axes L1 and L2. Further, screw 61 can be rotated 360 degrees about axis L at any one of the angular positions between axis L1 and L2. One specific example of a multi-axial screw having application with the present invention is described in U.S. Pat. Nos. 5,797,911 and 5,879,350, each of which is incorporated herein by reference.

In the illustrated example, anchor 60 includes a connector in the form of a generally cylindrical yoke 68 having passageway 70 therethrough for receiving brace 90. Head 63 of screw 61 is received within a bowl 69 formed at the bottom of yoke 68. A groove 67 is formed in bowl 69, and a collar 65 is retained in bowl 69 via groove 67. Collar 65 captures screw 61 in yoke 68, and is configured to mate with head 63 to allow multi-axial orientations of screw 61 as described above. A cap 66 is positioned over head 63 and limits upward displacement of screw 61 in yoke 68.

Yoke 68 includes arms 71 extending upwardly from bowl 69 on opposite sides of passageway 70. Arms 71 have internal threads 72 configured to mate with external threads 77 on set screw 76. Set screw 76 has upper tool engaging portion 78 having tool dimension d2 and a lower tool engaging portion 79 having tool dimension d1 that is less than d2. Set screw 76 has a shoulder 80 that is supported on inner sleeve 50 by lip 52. Set screw 76 is positioned with shoulder 80 on lip 52 by threading external threads 77 past lip 52. In FIG. 4, set screw 76 is partially threaded into internal threads 72 of yoke 68 in order to couple anchor 60 to anchor extension 30. Upper tool engaging portion 78 has a reduced thickness portion 81 where it joins lower tool engaging portion 79. Thus, in this embodiment, set screw 76 is a break-off type set screw which severs at reduced thickness portion 81 when a predetermined threshold torque is applied at upper tool engaging portion 78, thus allowing a desirable and uniform securing force to be applied to brace 90 with each of the set screws 76. Another advantage is that set screw 76 can be released from anchor extension 30 when set screw 76 is severed.

Yoke 68 is received within recess portion 42 at distal end 41 of outer sleeve 40. As shown in FIG. 5, an end view of outer sleeve 40, recess 42 is shaped with a generally cylindrical wall with a couple of flat surface to conform to the outer perimeter of yoke 68 at upper end surfaces 73. Upper surfaces 73 of arms 71 are held firmly against recessed surface 44 by set screw 76, which is releasably coupled to yoke 68 and inner sleeve 50, by drawing yoke 68 into recess 42 via inner sleeve 50. Anchor 60 is mounted to anchor extension 30 and held in a fixed position relative to anchor extension 30. Axis L3 of anchor extension 30 is aligned with axis L1 of bone screw 61 when a guidewire, such as guidewire 280 of FIG. 18, or a tool, such as tool 100 or 100' of FIGS. 20 and 20b is inserted into screw 61 to maintain anchor 60 in this aligned position.

Figure 6:
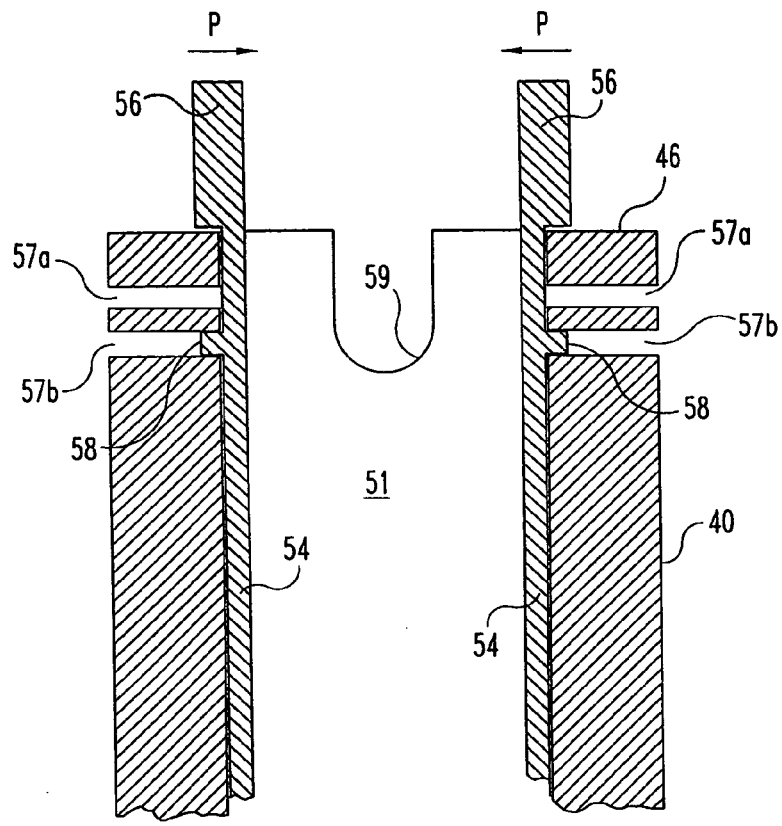
FIG. 6 is an enlarged section view of a portion of the installation instrument taken through line 6-6 of FIG. 1.
Figure 7:
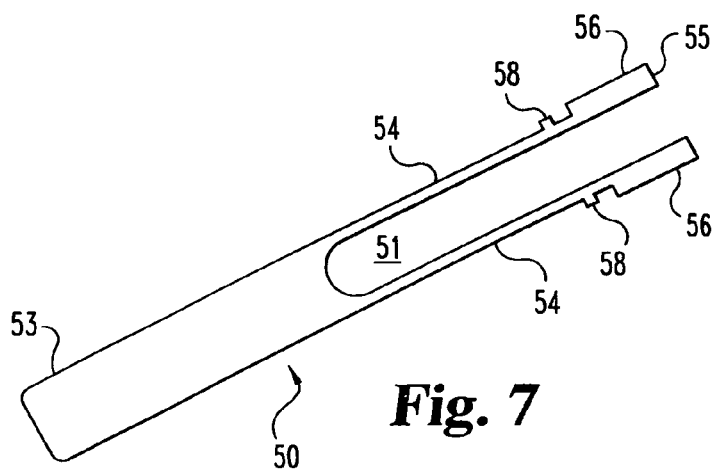
FIG. 7 is a perspective view on a much smaller scale than FIGS. 4 and 6 of an inner sleeve comprising a portion of the installation instrument of FIG. 1.

Referring to FIGS. 6 and 7, inner sleeve 50 and its connection with outer sleeve 40 will be further described. Inner sleeve 50 includes lower cylindrical tubular body portion 53. Fingers 54 extend from body portion 53 to upper end 55 of inner sleeve 50. Fingers 54 include retainers 56 adjacent upper end 55. A pin or nub 58 is positioned on and extends from the outer surface of each finger 54. Outer sleeve 40 includes upper paired holes 57a and lower paired holes 57b, which serve as catches. As shown in FIG. 6, nubs 58 are positionable within catches 57a or 57b formed in outer sleeve 40 to hold inner sleeve 50 relative to outer sleeve 40. Retainers 56 contact upper end 46 of outer sleeve 40 when nubs 58 are positioned in lower catches 57b. Retainers 56 limit the depth of insertion of inner sleeve 50 into bore 45 of outer sleeve 40. Retainers 56 also facilitate insertion and withdrawal of inner sleeve 50 relative to outer sleeve 40 by providing the surgeon means to grasp fingers 54 and squeeze.

Finger 54 can be deflected towards one another as indicated by arrows P in order to disengage nubs 58 from catches 57a and 57b, thus allowing rotation and axial translation of inner sleeve 50 in outer sleeve 40. Outer sleeve 40 includes notches 59 formed at upper end 46 on opposite sides of outer sleeve 40 between respective ones of the paired catches 57a and paired catches 57b. Notches 59 allow inner sleeve 50 to be positioned in outer sleeve 40 with nubs 58 at a depth approximating the location of catches 57a and 57b without deflecting fingers 54. Fingers 54 can then be pressed together to withdrawal nubs 58 from notches 59, allowing inner sleeve 50 to be rotated and nubs 58 positioned in the desired paired catches 57a or paired catches 57b.

With nubs 58 positioned in lower catches 57b, set screw 76 extends into recess portion 42 of outer sleeve 40 enough to allow anchor 60 to be mounted on extension 30 by threading set screw 76 partially into yoke 68. Nubs 58 can then be positioned in upper catches 57a, retracting yoke 68 into recessed portion 42 of outer sleeve 40 to hold anchor 60 firmly in place as shown in FIG. 4 and described above. Anchor 60 can thus be pre-assembled with anchor extension 30 before engaging anchors 60 to the bony structure, allowing the assembled anchor 60 and anchor extension 30 to be positioned percutaneously together in a minimally invasive approach to the bony structure. However, it is also contemplated that anchor extension 30 can be mounted on an anchor 60 that is already engaged to the bony structure.

Figure 8:
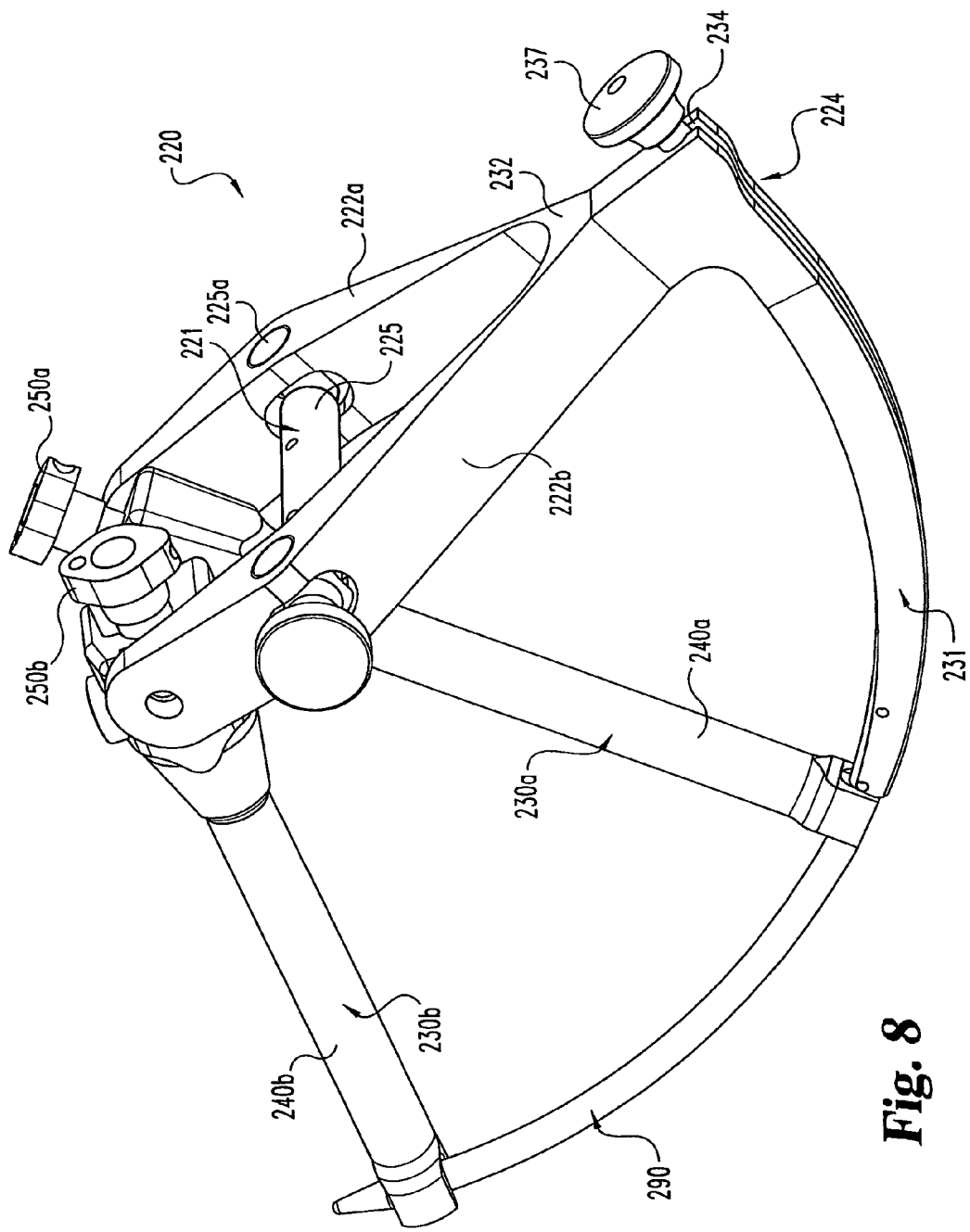
FIG. 8 is a perspective view of a further embodiment of a brave and an installation instrument according to the present invention.
Figure 9:
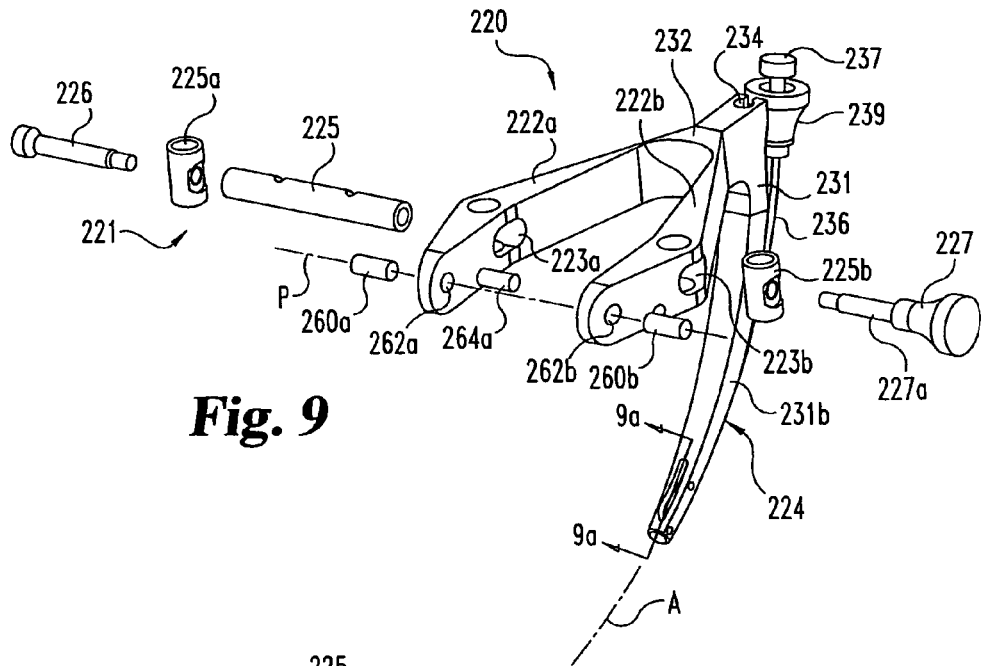
FIG. 9 is an exploded perspective view of a portion of the installation instrument of FIG. 8.

Referring now to FIGS. 8 and 9, another embodiment of an installation instrument is illustrated. In FIG. 9, anchor extensions 230 are not illustrated. Anchor extensions 230 include an inner sleeve 240 that is received proximally within outer sleeve 250 in a manner similar to that described above with respect to anchor extension 30. The inner sleeve 240 and outer sleeve 250 are further illustrated in FIGS. 14-17, and are described in further detail below.

Figure 9A:
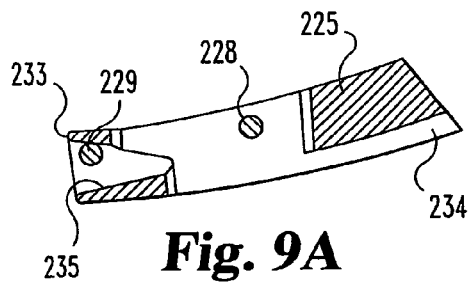
Figure 10:
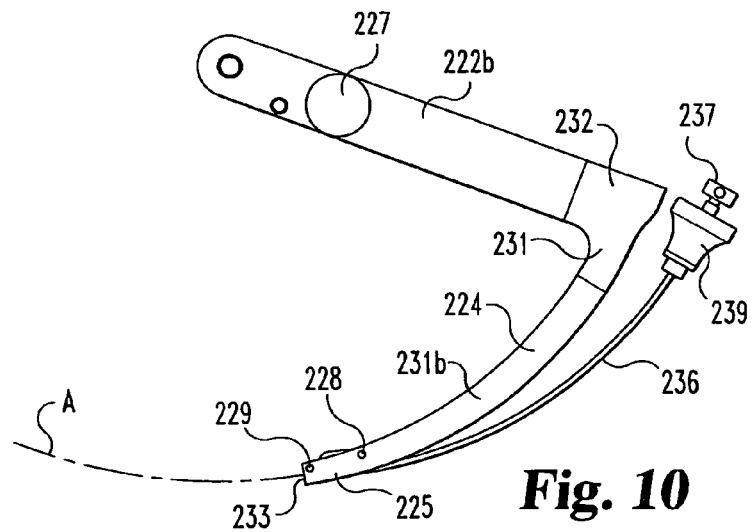
FIG. 10 is a side elevational view of the portion of the installation instrument of FIG. 9.

Installation instrument 220 includes a brace inserter 224 having a first support arm 222a and a second support arm 222b. Support arms 222a, 222b come together and are fixedly connected at a proximal end 232 of a pivot arm 231. Referring now further to FIGS. 9a and 10, pivot arm 231 includes a distal end 233 from which brace 290 extends. Brace inserter 224 includes a brace mounting portion 225 adjacent distal end 233 for securing a brace, such as brace 290, thereto. Brace 290 is similar to brace 90, and includes a connecting portion 291 as described further below. Brace inserter 224 is pivotable about a pivot axis P to define a curvilinear arc or axis A. Pivot arm 231 of brace inserter 224 is preferably curved along curved portion 231b to follow axis A and facilitate smooth percutaneous insertion and withdrawal of pivot arm 231. As shown in FIG. 9a, brace mounting portion 225 includes a brace receiving opening 235 extending proximally from distal end 233.

Pivot arm 231 includes a channel 234 extending from distal end 233 therealong towards proximal end 232. Channel 234 receives a brace coupler 236 therein that is secured to inserter 224 by a nut 239 and pin 228. For the purposes of clarity, nut 239 and brace coupler 236 are shown displaced from channel 234 except at distal end 233. Preferably, brace coupler 236 is an elongated flexible member that extends with arc axis A from distal end 233 through nut 239 to a set screw 237 adjacent proximal end 232. Coupler 236 is pivotably coupled to inserter 224 at brace mounting portion 225 via pin 228. Set screw 237 is threadingly received in a threaded opening formed in nut 239. Brace mounting portion 225 also includes stop pin 229 extending therethough in communication with brace receiving opening 235.

Figure 11:
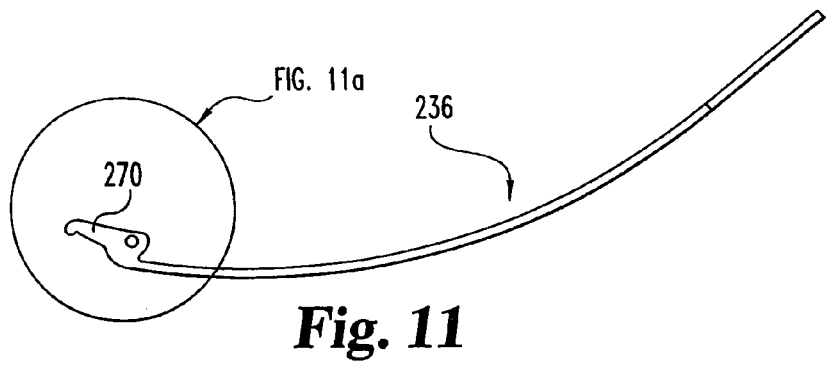
FIG. 11 is a side elevational view of the brace coupler of the installation instrument of FIG. 8.
Figure 11A:
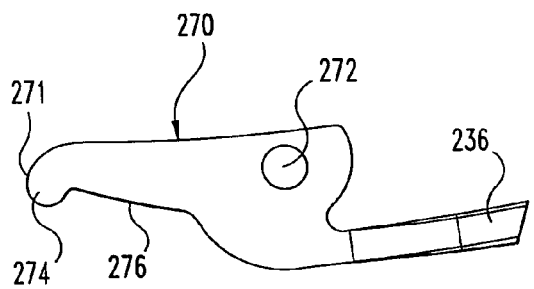
FIG. 11a is an enlarged detail view of a portion of the brace gripper of FIG. 10.
Figure 12:
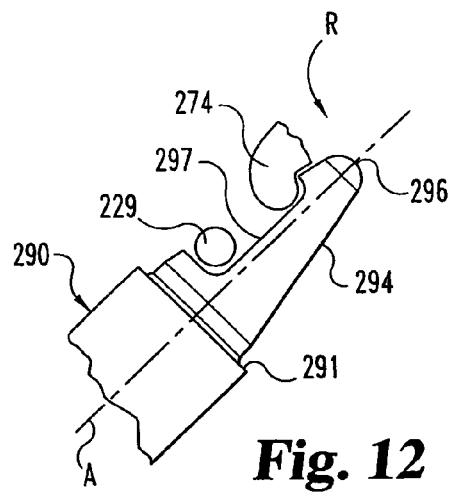
FIG. 12 is an enlarged detail view of the portion of installation instrument connected to an indexed brace.

Referring now further to FIGS. 11-12, brace 290 is positionable in brace receiving opening 235 so that brace 290 is relatively fixed with respect to inserter 224 by brace coupler 236, maintaining alignment of brace 290 along arc axis A during insertion of brace 290. Brace coupler 236 includes gripping portion 270 at its distal end for gripping brace 290. Gripping portion 270 has through-hole 272 receiving pin 228 therethrough and rotatably coupling gripping portion 270 at brace mounting portion 225. Gripping portion 270 further includes a tooth 274 extending therefrom at its distal end 271. A notch 276 extends proximally from tooth 274.

Brace 290 has a connecting end 291 with a connecting post 294 extending therefrom. Preferably, connecting post 294 is tapered from connecting end 291 to tip 296, and has a recess 297 with a length and depth configured to receive tooth 274 at the end of the recess 297 adjacent tip 296 and stop pin 229 at the end of recess 297 adjacent connecting end 291. Stop pin 229 contacts brace 290 in recess 297 to limit the depth of insertion of brace 290 into opening 235.

In one aspect of the invention, brace 290 is indexed by providing a single recess 297 at a predetermined location on post 294. Post 294 cannot be inserted properly into channel 235 unless stop pin 229 is received in recess 297, thus ensuring an orientation of brace 290 with respect to inserter 224 that is determined by the position of recess 297 with respect to stop pin 229. Preferably, the position of recess 297 is such that it is located with respect to gripping portion 270 so that the radius of curvature of brace 290 extends from inserter 224 along arc axis A. This ensures accurate positioning and orientation of brace 290 with respect to anchors 60 during installation of brace 290.

In order to grip brace 290 when connecting portion 291 is placed into opening 235, gripping portion 270 is rotated downwardly about pin 228 in the direction of arrow R by drawing brace coupler 236 proximally via threading of set screw 237 in a first direction with respect to lock nut 239. Set screw 237 is threaded in an opposite second direction to push brace coupler 236 distally and therefore bend coupler 236, rotating tooth 274 about pin 228 in the direction opposite arrow R out of recess 297 thereby releasing brace 290.

Referring back to FIGS. 8 and 9, support arms 222a and 222b have through-holes 223a, 223b for receiving a clamping mechanism 221. Clamping mechanism 221 draws arms 222a, 222b towards one another to pivotably secure anchor extensions 230a, 230b therebetween. Pivot nuts 225a and 225b are positionable in through holes 223a and 223b, respectively. A clamping bar 225 extends between arms 222a and 222b, and has threaded bores at each end that allow bar 225 to be secured to and clamp arms 222a, 222b via threaded fastener 226 and clamping knob 227 having a threaded stem 227a. Clamping knob 227 is manipulated by the surgeon to secure or release extensions 230a and 230b from arms 222a and 222b.

In the illustrated embodiment, pin 260a is press fit into opening 262a of arm 222a. Anchor extension 230a is rotatably mounted on support arm 222a via pin 260a. Similarly, anchor extension 230b is rotatably mounted on support arm 222b via pin 260b press fit into opening 262b of arm 222b. Other techniques for securing pins 260a, 260b and mounting extensions 30a, 30b thereto are also contemplated as would occur to those skilled in the art. Each arm 222a, 222b can be provided with a stop bar 264a, 264b extending therefrom towards the other support arm 222b, 222a, respectively. Stop bars 264a and 264b limit rotation of instrument 220 along axis A when stop bars 264a, 264b contact a corresponding one of the extensions 230a, 230b.

Figure 16:
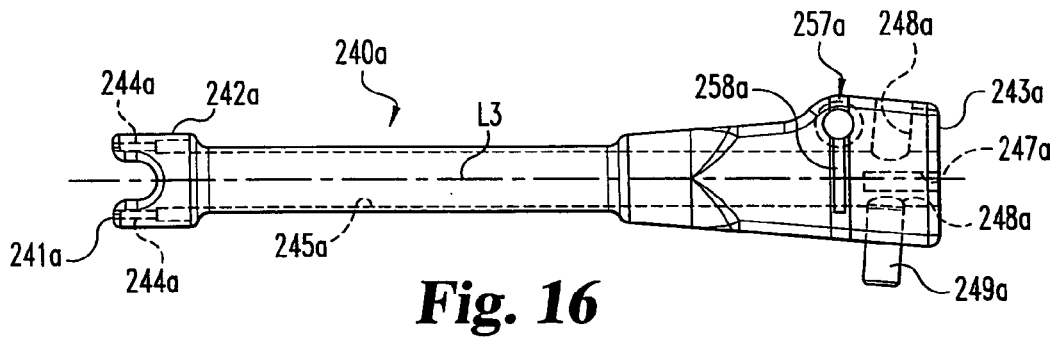
FIG. 16 is a side elevational view of a first outer sleeve forming a portion of the anchor extension of the installation instrument of FIG. 8.
Figure 17:
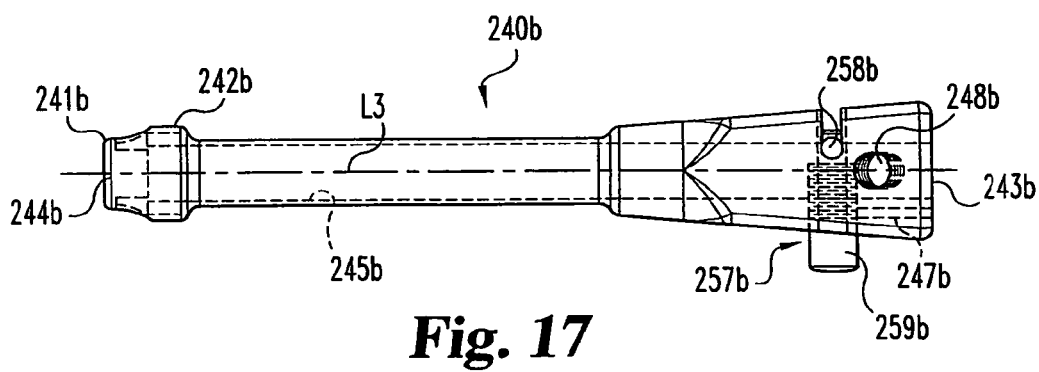
FIG. 17 is a side elevational view of a second outer sleeve forming a portion of the anchor extension of the installation instrument of FIG. 8 rotated 90 degrees about its longitudinal axis as compared with the first outer sleeve of FIG. 16.

Referring now to FIGS. 14-17, anchor extensions 230 that coupled to inserter 224 will now be described in further detail. These anchor extensions 230 are illustrated in an assembled condition in FIG. 8. It should be noted that second outer sleeve 240b of FIG. 17 is illustrated rotated 90 degrees about its longitudinal axis as compared with the orientation of the elevational view of first outer sleeve 240a of FIG. 16.

Although anchors are not shown in FIG. 8, anchor extension 230a can have mounted thereon at its lower or distal end a first anchor, such as anchor 60a described above. Similarly, anchor 230b can have mounted at its lower or distal end a second anchor, such as anchor 60b, described above. Anchor extensions 230a, 230b, collectively referred to as anchor extensions 230, each include outer sleeve 240 and an inner sleeve 250 disposed within a bore 245 through outer sleeve 240. Inner sleeve 250 defines a bore 251 therethrough that allows tools to extend into the anchor. Distal end 253 of inner sleeve 250 includes a lip 252 extending radially therearound projecting into inner bore 251. Lip 252 supports a set screw, such as set screw 76 described above, on the distal end of inner sleeve 250.

Yoke 68 is preferably received within end portion 242 at distal end 241 of outer sleeve 240. As shown in FIG. 16, end portion 242 has a U-shaped opening that is alignable with passageway 70 to accommodate insertion of brace 290 therethrough. The arms 244 of end portion 242 are alignable with the arms 71 of yoke 68, receiving arms 71 therein, firmly securing anchor 60 onto anchor extension 230 during insertion of the anchor.

The positioning of inner sleeve 250 into outer sleeve 240 will be further described, although those skilled in the art will appreciate that anchor extension 30 and anchor extension 230 are similar in many respects. Inner sleeve 250 includes lower gripping elements or fingers 254 that include circular relief portions 277 therebetween to allow flexing of fingers 254. Inner sleeve 250 further includes upper notch 256 and lower notch 256' between fingers 254 and upper end 255. Outer sleeve 240 includes a plunger-type spring biased retainer 257 extending therein adjacent bore 245 having a cross bar 258 extending transversely from a plunger 259. Cross bar 258 is selectively positionable in a desired one of the notches 256 and 256' to hold inner sleeve 250 relative to outer sleeve 240. Shoulder 261 limits the depth of travel of inner sleeve 250 distally into bore 245 of outer sleeve 240. When cross bar 258 is in upper notch 256, set screw 76 of anchor 60 can be threaded onto or pushed between fingers 254 at distal end 253, where set screw 76 is retained thereon by lip 252.

If not already secured to set screw 76, yoke 68 can then be at least partially threaded onto set screw 76. Movement of inner sleeve 250 relative to outer sleeve 240 is facilitated by depressing plunger 259 to lift cross bar 258 out of upper notch 256. Inner sleeve 250 is moved proximally to position cross bar 258 in lower notch 256', drawing yoke 68 between the arms 244 and against end portion 242 with passage 70 aligned with the U-shaped opening between the arms 244. Axis L3 of anchor extension 230 is aligned with axis L1 of bone screw 61 when a guidewire or a tool, such as tool 100 or 100' of FIGS. 20 and 20b is inserted into screw 61 to maintain anchor 60 in this aligned position. An alignment pin 263 of inner sleeve 250 is received in slot 249 of outer sleeve 240 to ensure and maintain proper alignment of inner sleeve 250 in outer sleeve 240.

The assembly of anchor extensions 230a and 230b to one another and also to inserter 224 will now be described. Each anchor extension 230 includes passage 248 through outer sleeve 240 adjacent the proximal end 243. A coupling pin 249a is press fit or otherwise secured in passage 248a on the side of anchor extension 230a adjacent anchor extension 230b. After anchor extensions 230a and 230b and anchors 60a and 60b are secured to bony structure, anchor extensions 230a and 230b are manipulated through the skin and tissue to place pin 249a into the portion of passage 248b adjacent anchor extension 230a. Inserter 224 is secured to anchor extensions 230a and 230b by placing pin 260a in a portion of passage 248a of first extension 230a opposite pin 249a, and pin 260b in a portion of passage 248b of second extension 230b opposite pin 249a. Pins 260a and 260b are rotatably received in the passages 248a and 248b, respectively, and anchors extension 230a and 230b are secured to support arms 222a and 222b via clamping mechanism 221. Bores 251a and 251b of inner sleeves 250a and 250b remain substantially unobstructed for access to anchors 60a and 60b when instrument 220 is assembled.

Techniques using the above described installation instruments 20, 220 will now be described. The present invention contemplates that placement of anchors 60 into the bony structure can be completed without an anchor extension 30 or 230 mounted thereto, and anchor extension 30 or 230 is thereafter mounted on the anchor 60 engaged to the bony structure. Other techniques contemplate that the anchor 60 is mounted on anchor extension 30 or 230, and anchor extension 30 or 230 and anchor 60 are placed through an open incision, micro-incision, a tube or cannula, or directly through the skin and tissue of the animal subject to engage anchor 60 to a bony structure, such as the pedicles of vertebrae V1 and V2 as shown in FIG. 1.

The surgical techniques of the present invention can employ any type of known imaging system to determine and locate optimum placement and orientation of the anchors in the bony structure and, if necessary, to locate skin locations for percutaneous puncture entry of the anchors. Image guided systems useful in practicing the invention and in placing anchors 60 are known in the art. Examples of image guided technology are provided in U.S. Pat. No. 5,772,594; U.S. Pat. No. 5,383,454; U.S. Pat. No. 5,851,183; U.S. Pat. No. 5,871,445; U.S. Pat. No. 5,891,034; and PCT Publication WO 99/15097, each of which is incorporated herein by reference in its entirety. The STEALTHSTATION® or ION™ systems, sold by Medtronic Surgical Navigation Technologies, Inc. can further be used with the present invention for pre-operative planning and image guided navigation of anchor placement and installation of brace 90.

Other techniques for locating and placing anchors 60 into the bony structure are also contemplated herein as would occur to those skilled in the art. For example, a CT scan or x-ray can be used for pre-operative planning of anchor positioning and orientation. Anchor insertion can be monitored using any known viewing instrument or apparatus. Another example contemplates anchor placement through a cannula or sleeve inserted through the skin that forms a working channel to the anchor location. Anchor placement into the bony structure can be monitored endoscopically or microscopically through the cannula.

In one specific technique, a guidewire, such as guidewire 280 of FIG. 18, of sufficient length is inserted percutaneously and anchored to the bony structure. The guidewire is coupled to a trackable instrument that is tracked via an image guided surgical system that generates a display on a computer monitor. Further examples of such instruments and systems are described in further detail in PCT Publications WO 99/15097 and WO 99/26549, each of which is incorporated herein by reference in its entirety. With the guidewire secured at the appropriate location on the bony structure, various instruments for preparing and inserting the screw into the bony structure can be guided by the guidewire. The preparation and insertion can be monitored via a tracking instrument coupled to the various preparation and insertion instruments.

Various instruments can be used to prepare the surgical site for anchor insertion. For example, in FIG. 19 there is illustrated a cannulated awl 300 that is inserted over the guidewire to prepare the bony structure for screw insertion. Awl 300 has a bore 306 extending between distal end 303 and proximal end 302 that allows awl 300 to be inserted over the guidewire. Awl 300 is configured at proximal end 302 to engage a driving instrument, which can also include a tracking instrument to monitor insertion depth. Awl 300 has shaft 304 extending to distal end 303. A cutting head 307 at distal end 303 prepares a hole in the bony structure for the anchor.

After determining the desired position and orientation of guidewire 280 in the bony structure and the skin location for puncture entry and preparing the screw hole, a cannulated anchor 60 mounted on anchor extension 30 or 230 can be placed over the guidewire and advanced, for example, through the skin and tissue directly, through an incision, or through a cannula to the prepared hole. A driving tool, such as cannulated driving tool 100' shown in FIG. 20a, is used to threadingly engage anchor 60 to the bony structure. Cannulated tool 100' includes bore 106' extending between proximal end 102' and distal end 103'. Distal end 103' includes an engaging portion 107' to mate in tool engagement recess 64 of screw 61. Tool 100' is placed over the guidewire and through the tool bores of the anchor extensions 30, 230 to drive the cannulated screw 61 into the bony structure.

It is further contemplated that if the technique does not employ a guidewire, a driving tool 100 of FIG. 20b can be inserted through the tool bores of the anchor extensions 30, 230 to screw 61. Tool 100 includes proximal end 102 and a shaft 104 extending to distal end 103. Proximal end 102 is preferably configured to engage a wrench or handle to facilitate application of a driving force with tool 100. Distal end 103 includes a lower engaging portion 107 having a length configured to mate in tool engagement recess 64 of screw 61 to drive screw 61 into the bony structure.

Anchor extension 30, 230 follows anchor 60 towards the bony structure as anchor 60 is driven therein with driving tool 100 or 100'. Tool 100 is then withdrawn from the tool bore, and if necessary, the guidewire is also withdrawn. In embodiments of anchor 60 having a multi-axial screw, yoke 68 and anchor extension 30, 230 are pivotable about head 63 by manipulating anchor extension 30, 230 in the skin and tissue to the desired position.

With anchors 60a and 60b secured to the bony structure, passageways 70a and 70b are aligned to receive brace 90. For instrument 20, upper posts 28a and 28b are mounted on anchor extensions 30a and 30b using thumb screws 27a and 27b, respectively, aligning passageways 70a and 70b. With anchors 60 employing a multi-axial screw, the anchor extensions 30a and 30b can be manipulated into the desired position for connection with upper posts 28a and 28b. For instrument 220, anchor extensions 230a and 230b are manipulated to place pin 249a in passage 248b, aligning passageways 70a and 70b. Support arms 222a and 222b are secured to anchor extensions 230a and 230b with clamping mechanism 220. If anchor 60 does not have multi-axial capabilities, the orientation of the anchor extensions required to connect the inserter thereto is accounted for during the determination of the orientation and positioning anchors 60a and 60b into the bony structure.

Brace 90, 290 is fixed on inserter 24, 224 and readied for percutaneous insertion into passageways 70a and 70b of anchors 60a and 60b, respectively. Preferably, brace 90, 290 is curved and has a radius of curvature equal to the distance between passageways 70a, 70b and pivot axis P. Inserter 24, 224 swings about pivot axis P to move brace 90 in a forward direction along arc axis A and thereby introducing pointed end of brace 90, 290 into the subject's body towards the aligned passageways 70a and 70b. Brace 90, 290 and inserter 24, 224 are further pivoted to pass portions of brace 90 through passageways 70a and 70b of anchors 60a and 60b.

Figure 13:
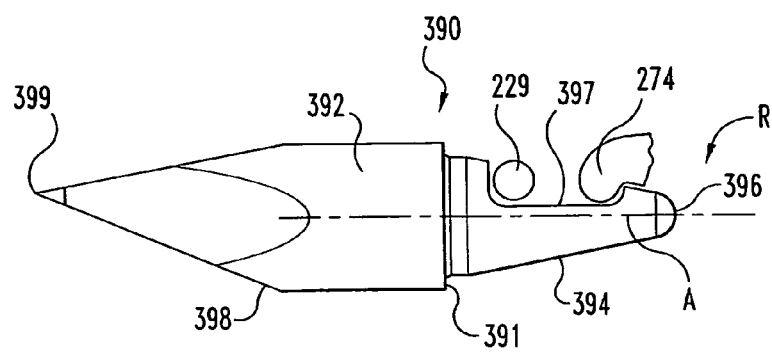
FIG. 13 is an enlarged view of a trocar and the portion of the installation instrument connected thereto.
Figure 14:
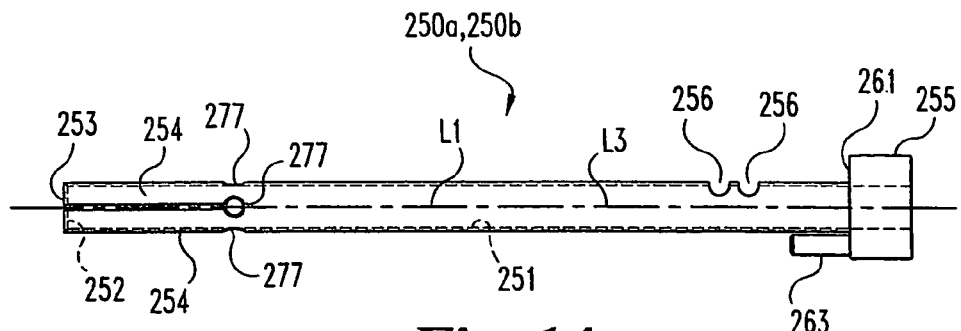
FIG. 14 is an elevational view of an inner sleeve forming a portion of the anchor extension of the installation instrument of FIG. 8.
Figure 15:
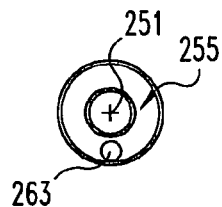
FIG. 15 is a right hand end view of the inner sleeve of FIG. 14.

As discussed above, it is preferred that brace is indexed so that it can be secured at a predetermined orientation onto the installation instrument 20, 220. This ensures alignment of brace 90, 290 along the insertion path of the installation instrument and through the passageways of anchors 60a and 60b. In a further form, trocar 390, as shown in FIG. 13, can be used to puncture skin and tissue along the insertion path and facilitate insertion of brace 90, 290 in a percutaneous procedure. Trocar 390 has a connecting end 394 identical to that of brace 290. However, trocar 390 has a short shaft 392 extending to puncture tip 398. Puncture tip 398 has a sharp point 399 to facilitate insertion and create a pathway through skin and tissue of the patient.

Brace 90, 290 is placed through the passageways of anchors 60a and 60b to the desired position, which can be confirmed radiographically or with any know imaging technique. Set screws 76a and 76b of each anchor 60a and 60b are driven downward to contact brace 90, 290. A driving tool is placed through the tool bores of the installation instruments 20, 220 to engage either the upper tool engagement portion 78a, 78b or lower tool engagement portion 79a, 79b and drive set screw 76a, 76b downwardly, tightening it against brace 90, 290 until set screw 76a, 76b is firmly seated thereagainst. Inserter 24, 224 can then be uncoupled from brace 90, 290 and removed from the subject by swinging inserter 24, 224 back along arc axis A. A tool is positioned in upper tool engagement portion 78a, 78b to break off the upper portion of the set screw 76a, 76b upon application of the requisite torque, releasing the anchor extension 30a, 30b from anchor 60a, 60b and allowing removal of extensions 30, 230 from the subject.

The surgeon may also desire to initially seat set screw 76a, 76b using a tool in upper tool engagement portion 78a, 78b and apply sufficient torque to severe the break-off portion of set screw 76a 76b before uncoupling brace 90, 290. In an alternate form, the driving force that is applied to set screw 76a, 76b could force shoulder 80a, 80b through lip 52a, 52b, deflecting lip 52a, 52b downward to release set screw 76a, 76b from inner sleeve 50a, 50b of instrument 20 or deflect fingers 154a, 154b outward to release set screw 76a, 76b from inner sleeve 150a, 150b of instrument 220.

Figure 21:
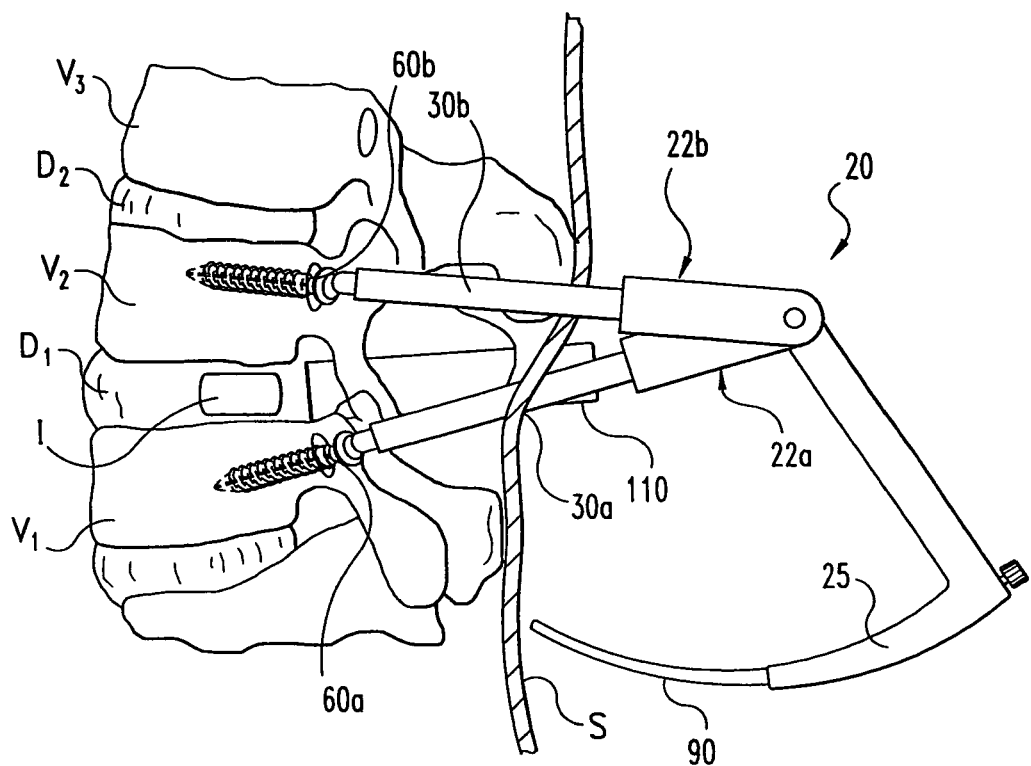
FIG. 21 is a side elevational view of a portion of the spinal column and the installation instrument along with a cannula for performing surgical procedures in the disc space.

In one specific application of the present invention, brace 90 is installed to stabilize a first vertebra V1 and second vertebra V2 after placement of one or more implants I into disc space D as shown in FIG. 21. The method includes removing the intervertebral disc from the space between first and second vertebral bodies through one percutaneous puncture in the subject. An implant I is introduced into the disc space. Implant I is preferably one or more interbody fusion devices or the like as is known in the art. The first and second anchors 60a and 60b and anchor extensions 30a and 30b are engaged to the first and second vertebral bodies, respectively, through second and third percutaneous punctures in the subject as described above. If desired, the anchor extensions 30 can be manipulated by the surgeon to apply a load to compress or distract the vertebrae prior to installing brace 90. Brace 90 is installed through a fourth percutaneous puncture in the subject using installation instrument 20 and secured to anchors 60a, 60b as described above. In some surgical procedures, it may be desirable to insert one or more additional braces to stabilize the bony structure using the above described installation instrument and techniques.

The present invention has application in further minimally invasive and open techniques for placing interbody fusion device into a disc space between adjacent vertebrae. For example, transforaminal, posterior, and posterior-midline approaches to the disc space are contemplated for placement of one or more implants or interbody fusion device in the disc space. Examples of such techniques are described in U.S. patent application Ser. No. 09/692,932, filed on Oct. 20, 2000. The present invention further has application for engagement of one or more rigid elongated connecting elements to one or more anchors for stabilization of a motion segment without fusion of the motion segment. The present invention also has application for engagement of one or more flexible elongated connecting elements to one or more anchors for stabilization of a motion segment without fusion of the motion segment.

Figure 22:
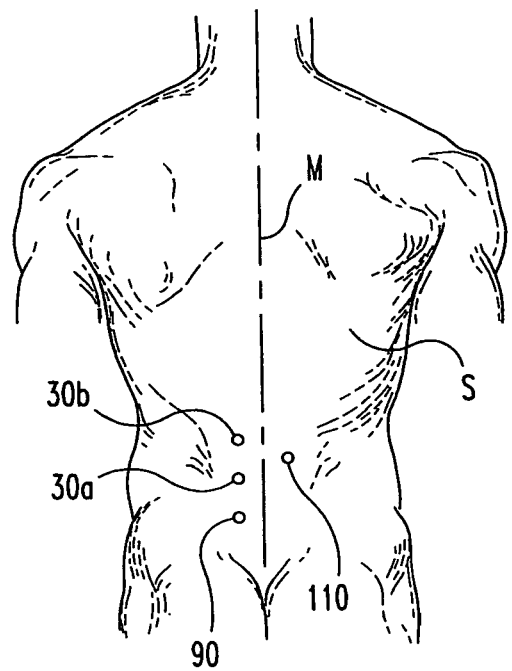
FIG. 22 is a top plan view of the instruments of FIG. 21 at the skin level.

As shown in FIG. 21, installation instrument 20 is mounted on anchors 60a and 60b engaged to vertebrae V1 and V2, respectively. Brace 90 is shown before percutaneous insertion. A cannula 110 is percutaneously inserted to a position adjacent disc space D1. As shown in FIG. 22, a plan view taken at skin surface S, first and second anchor extensions 30a, 30b and brace 90 are positioned on one side of midline M of the spine. Cannula 110 is positioned on the opposite side of midline M. One or more interbody fusion devices, bone graft material, or other material or implants are placed in the disc space. The adjacent vertebrae V1 and V2 are then stabilized by installing brace 90 as described above. Thus, a minimally invasive surgical procedure of the present invention contemplates interbody fusion and stabilization of the adjacent vertebrae to be accomplished with four entry holes or punctures through skin S.

The installation instrument of the present invention can also be used to install braces on both sides of midline M of the spine. The installation instrument can also be used to install multiple braces at one or more levels of the spine. The present invention can be used to stabilize adjacent vertebra in conjunction with any minimally invasive or open surgical techniques for placement of one or more interbody fusion devices into a disc space as would occur to those skilled in the art. For example, one or more interbody fusion devices or intervertebral spacers may be inserted into the disc space via an anterior approach. Examples of anterior approaches are described in PCT International Publication No. WO 97/30666; pending U.S. patent application Ser. No. 09/287,917; and pending U.S. patent application Ser. No. 09/498,426 filed on Feb. 4, 2000; each of which is incorporated herein by reference in its entirety. Further, the present invention may also be used to stabilize adjacent vertebrae, or any other bony structure, without placement of fusion devices or implants in the bony structure.

Figure 23:
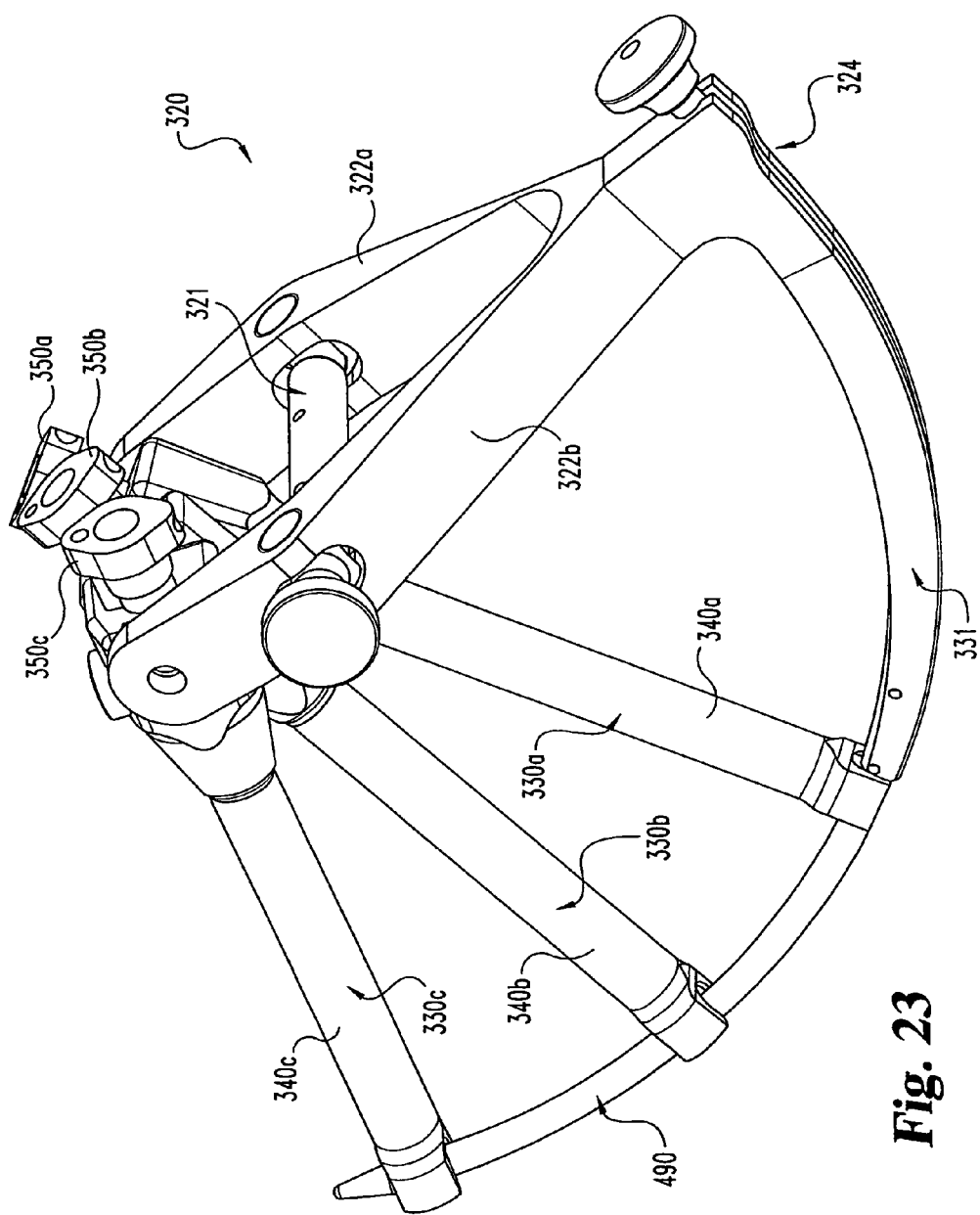
FIGS. 23 and 24 are perspective views of another embodiment of an installation instrument of the present invention usable in a two level stabilization procedure.
Figure 24:
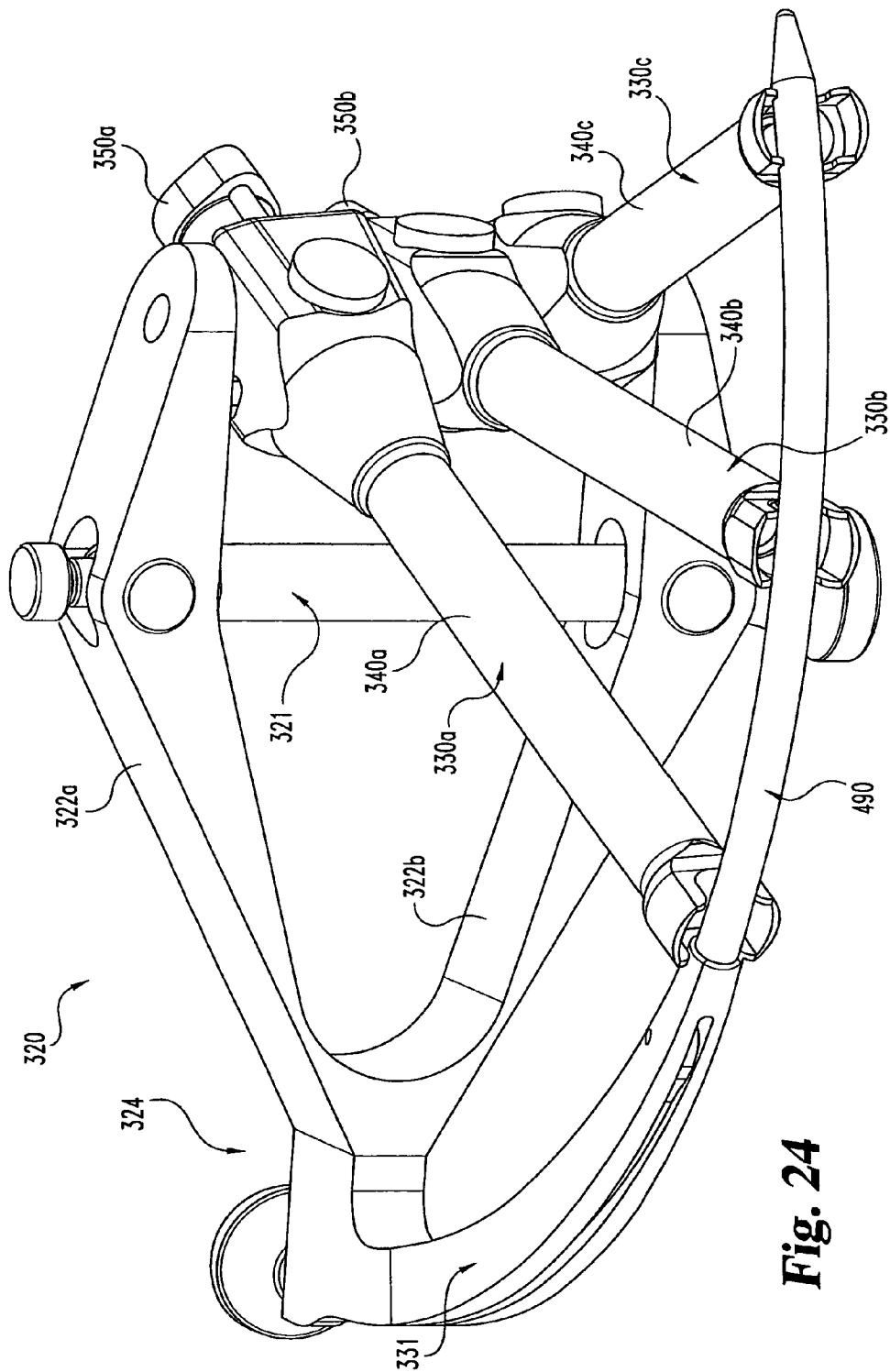

It is further contemplated that brace 90 may be installed and secured to anchors engaged in respective ones of three vertebrae using an installation instrument such as the one illustrated in FIGS. 23-24 and designated generally at 320. Instrument 320 is similar to and functions principally the same as instrument 220, except instrument 320 has a size and configuration adapted for this two level stabilization procedure. In this embodiment, three anchors that are like anchor 60 (not shown) are engageable to respective ones of three vertebrae or other bony structure using any of the above described techniques. Three anchor extensions 330a, 330b, 330c each include outer sleeves 340a, 340b, 340c and inner sleeves 350a, 350b, 350c that are substantially the same as outer sleeve 240 and inner sleeve 250 of instrument 220. Anchor extensions 330 are each mounted on a corresponding one of the three anchors. After the anchors are engaged to the bony structure, the three anchor extensions 330a, 330b, 330c are manipulated through the skin and coupled to one another in the same manner as described above with respect to anchor extensions 230a and 230b. Support arms 322a, 322b of inserter 324 are then rotatably mounted on the anchor extensions 330a, 330b, and 330c and clamped via clamping mechanism 321. Support arms 322a, 322b and clamping mechanism 321 are similar to support arms 222a, 222b and clamping mechanism 221 of installation instrument 220 except that each is sized to accommodate three anchor extensions 330 therebetween. An indexed brace 490 is similar to brace 290 and has a sufficient length for a two-level stabilization procedure. Brace 490 is secured to pivot arm 331 and then inserted through the passageways of the anchors as described above with respect to installation instrument 220.

Figure 25A:
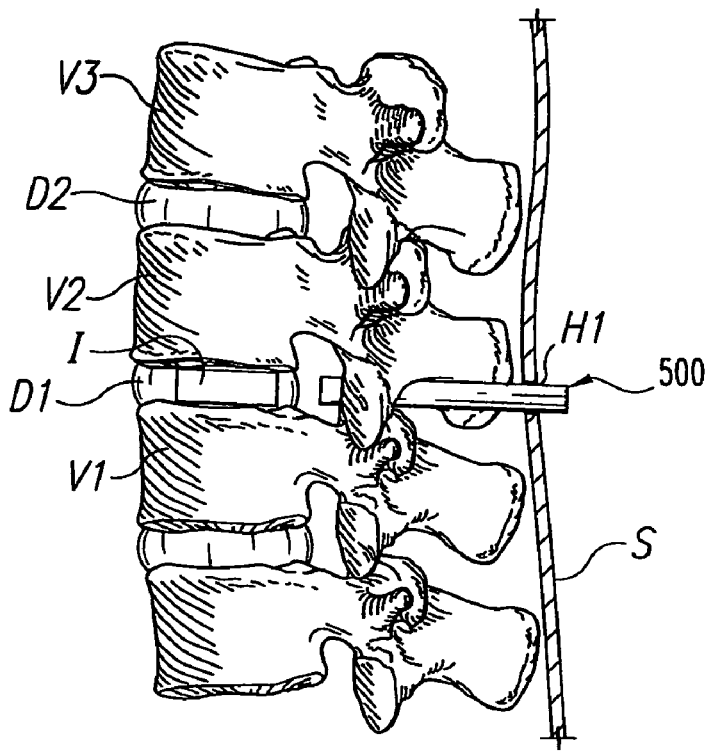
FIGS. 25a-25g illustrate various steps of a minimally invasive surgical procedure according to the present invention.

With reference to FIGS. 25a-25g, further description of minimally invasive surgical techniques will be provided. It should be understood that although surgical techniques described with reference to FIGS. 25a-25g make specific reference to installation instrument 220 with brace inserter 224 and anchor extensions 230, the other embodiment installation instruments discussed herein are also contemplated with such techniques. Furthermore, thought the technique is described with reference to first and second vertebrae V1 and V2, it should be understood that the techniques described herein have application with other bony structures and elements of the body. In FIG. 25a an incision H1 has been made through the skin and tissue of the patient in order to provide access to disc space D1 between vertebrae V1 and V2. In the illustrated embodiment, incision H1 is made for a posterolateral approach to the disc space, although transforaminal, posterior, and posterior-midline, lateral, antero-lateral and anterior approaches to the disc space are also contemplated. A retractor sleeve 500 is positioned through incision H1 to provide access to disc space D1 for performing surgical procedures in and/or adjacent to the disc space and vertebrae V1 and V2. Surgical procedures such as a laminotomy, laminectomy, foramenotomy, facetectomy and/or discectomy can be performed through retractor sleeve 500. A spinal fusion device, artificial disc or other interbody device indicated by implant I can also be inserted in the disc space through retractor sleeve 500. Examples of retractor sleeves and surgical approaches to the spinal disc space for inserting an implant or fusion device in the disc space through a retractor sleeve are provided in U.S. patent application Ser. No. 09/692,932 filed on Oct. 20, 2000 and also in U.S. patent application Ser. No. 09/815,963 filed on Mar. 13, 2001, each of which is incorporated herein by reference in its entirety.

In one specific procedure, it is contemplated that a needle having a stylet is inserted through the skin and tissue of the patient and entered into the bone at the desired location. The stylet is removed from the needle, and a guide wire inserted through the central needle bore and anchored to the bone. The needle is then withdrawn, and sequential dilation of the tissue is completed over the guidewire using one or more tissue dilators of increasing size. The retractor sleeve is then placed over the last inserted dilator.

Such procedures in disc space D1 through retractor sleeve 500 are considered to be minimally invasive because the cutting and retraction of muscle and soft tissue required to access disc space D1 and vertebrae V1 and V2 is minimized. The muscle and other tissue below skin S is sequentially dilated or retracted through incision H1 to separate the muscle and tissue and provide a pathway for insertion of retractor sleeve 500. Alternatively, retractor sleeve 500 can be configured to retract the muscle and tissue through incision H1 to accommodate its insertion and also after its insertion. Thus, the size of incision H1 is minimized to the size needed to accommodate retractor sleeve 500. For example, in one surgical technique, incision H1 has a length in the direction of the central axis of the spinal column that is the same as the cross sectional dimension as retractor sleeve 500. In one embodiment, incision H1 is 18 millimeters or less. In another embodiment, incision H1 is 16 millimeters or less. In a further embodiment, incision H1 is 14 millimeters or less.

Figure 25B:
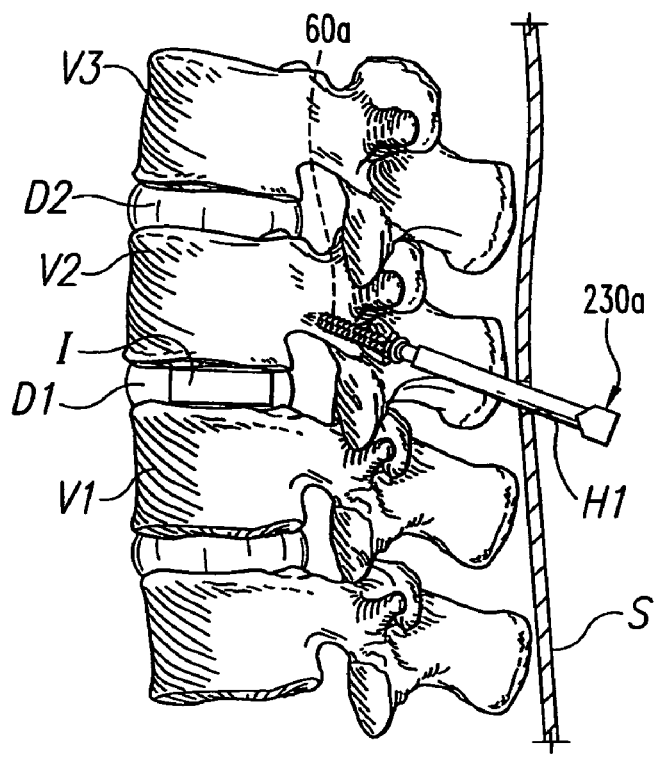
Figure 25C:
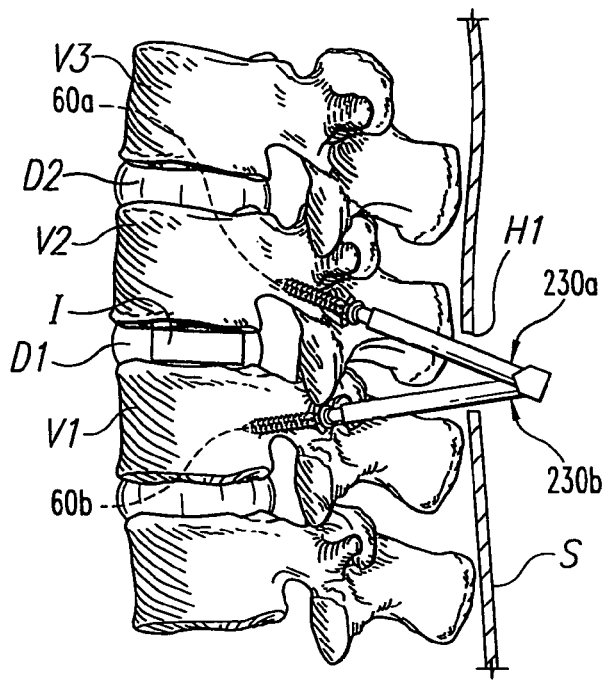

As shown in FIG. 25b, once the desired surgical procedures through retractor sleeve 500 have been completed, retractor sleeve 500 can be withdrawn from incision H1. Anchor 60a and anchor extension 230a are secured to vertebrae V2 using the techniques described herein. For example, a guidewire can be anchored to a desired location on vertebra V2 using lateral fluoroscopy or other image guidance instrumentation, and anchor 60a and anchor extension 230a are placed over the guidewire and anchor 60a secured to vertebra V2. Alternatively, anchor 60a and anchor extension 230a could be percutaneously guided through incision H1 and engaged to vertebra V2. As shown in FIG. 25c, anchor 60b and anchor extension 230b can be similarly secured to vertebra V1.

Figure 25D:
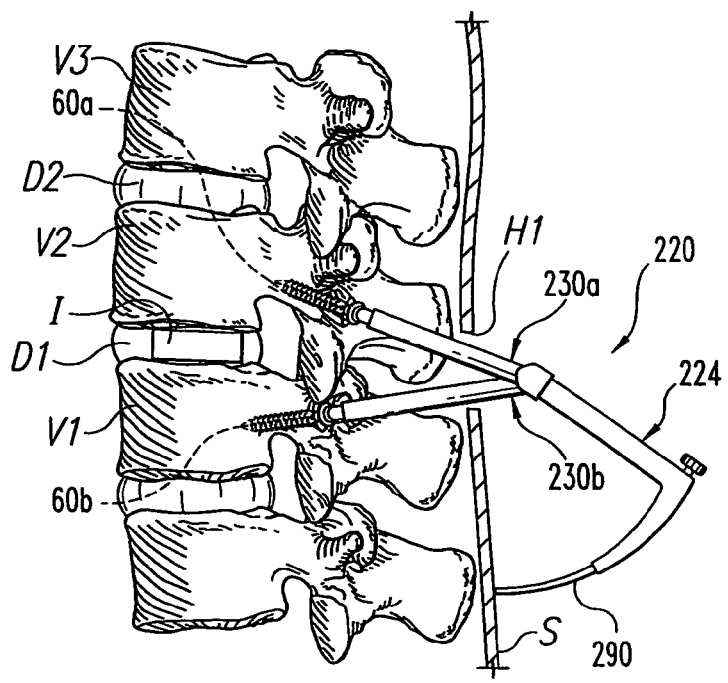
Figure 25E:
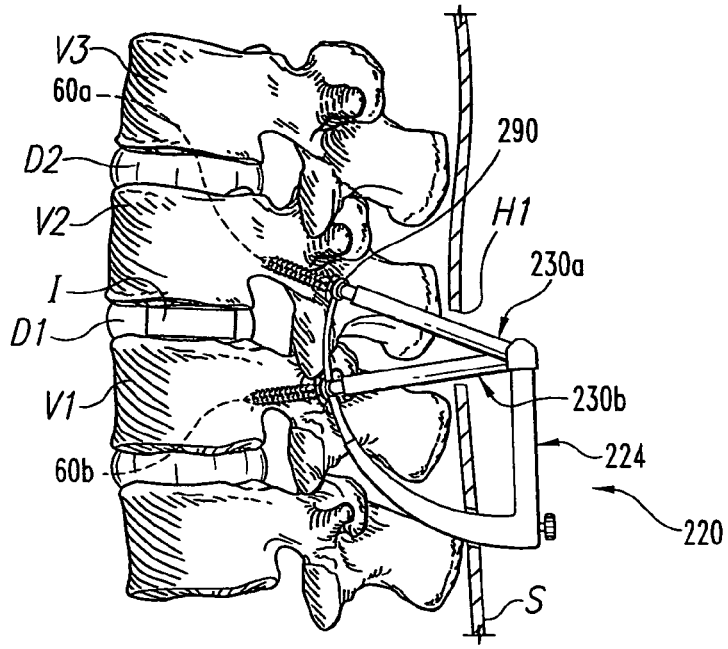
Figure 25F:
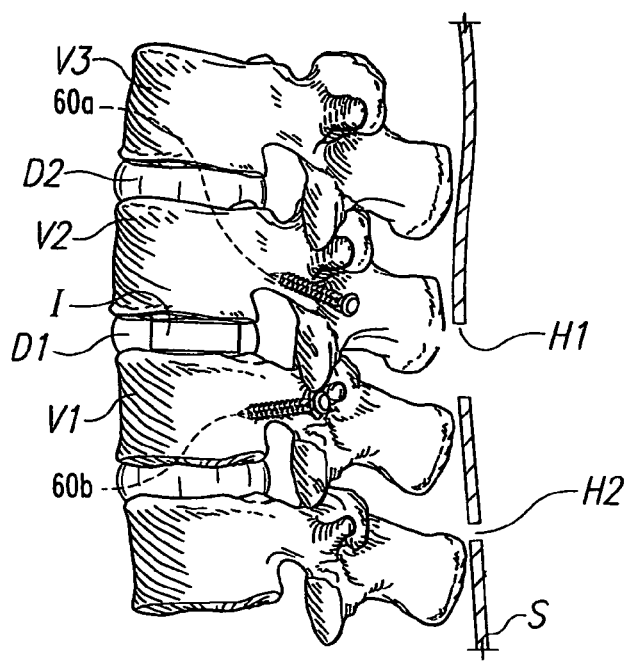
Figure 25G:
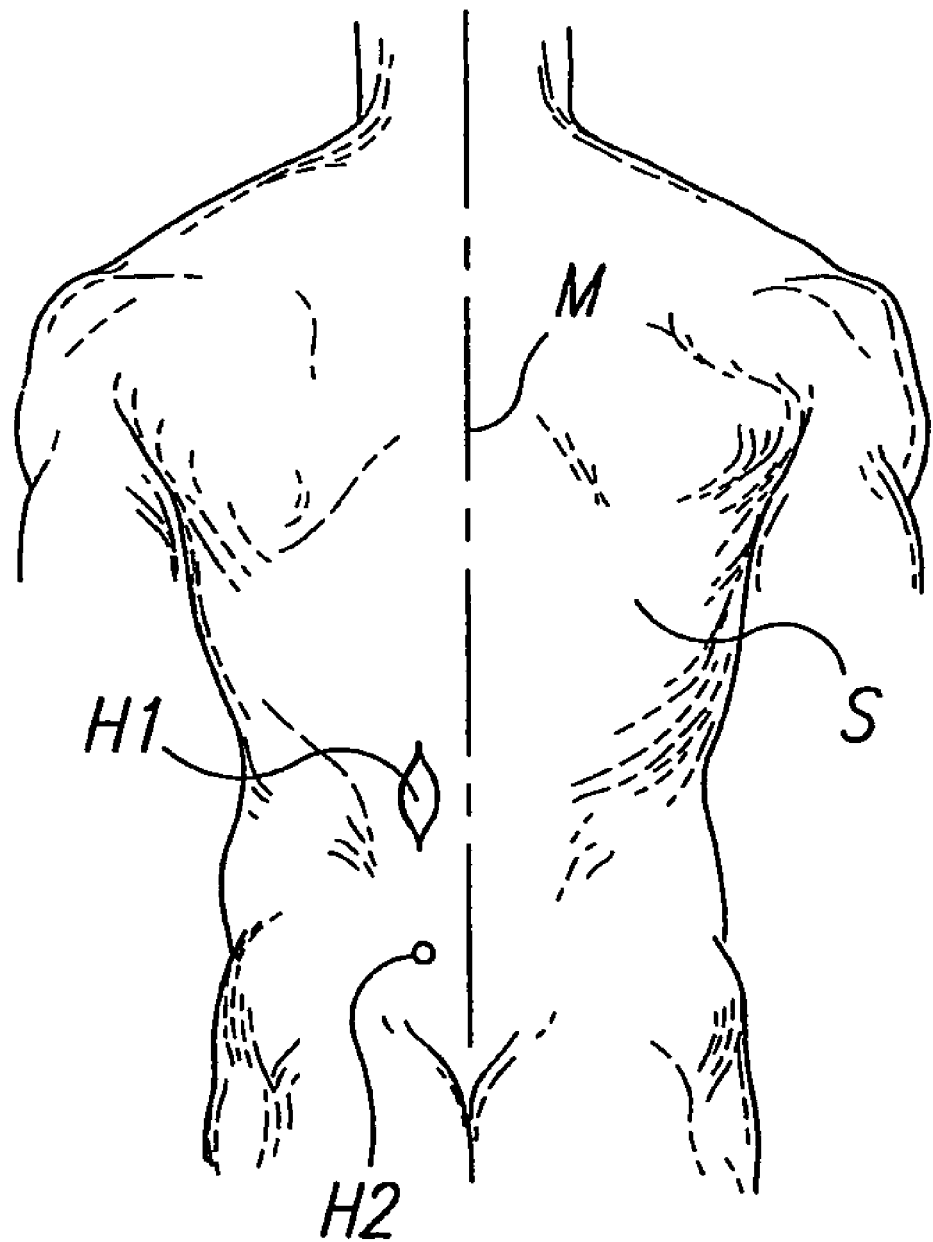

In FIG. 25d, inserter 224 of installation instrument 220 is mounted on anchor extensions 230a and 230b. Connecting element or brace 290 is coupled to inserter 224, and is shown in a position adjacent skin S of the patient before percutaneous insertion of connecting element 290. In FIG. 25e, brace 290 is percutaneously inserted and passed through passageways defined by receiving portions on anchors 60a and 60b. Brace 290 is then secured to anchors 60a and 60b with set screws. In FIG. 25f, inserter 224 and anchor extensions 230a, 230b of installation instrument 220 are removed. As also shown in FIG. 25g, the entry location of connecting element 290 forms a puncture wound H2 that is spaced and remote from incision H1.

The surgical technique provides for surgical treatment and/or stabilization of at least vertebrae V1 and V2. Surgical procedures are performed in or adjacent vertebrae V1 and V2 through retractor sleeve 500. Anchors 60a, 60b are engaged to vertebrae V2 and V1, respectively, through the same incision H1. The adjacent vertebrae V1 and V2 are stabilized by installing brace 290 through puncture wound H2. Thus, a minimally invasive surgical technique is provided the only requires an incision for surgical procedures in or adjacent to the disc space and vertebrae V1 and V2, and a puncture would for stabilization of vertebrae V1 and V2 with a connecting element.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A minimally invasive surgical method, comprising:
    making an incision in a patient for accessing first and second bony elements;
    placing through the incision first and second anchors coupled to first and second anchor extensions, respectively;
    engaging the first and second anchors to the first and second bony elements, respectively;
    mounting an inserter instrument on the first and second anchor extensions, the inserter instrument having a pivot axis relative to the anchors and further including a connecting element mounted thereon;
    swinging the inserter instrument relative to the anchors about the pivot axis and thereby moving the connecting element through an arc centered on the pivot axis of the inserter instrument;
    introducing an end of the connecting element into the patient from a location remote from the incision; and
    positioning the connecting element proximate to the first and second anchors.

2. The method of claim 1, wherein placing first and second anchors includes placing the first and second anchors percutaneously through the incision.

3. The method of claim 2, wherein introducing the end of the connecting element includes introducing the end of the connecting element percutaneously at the location.

4. The method of claim 1, further comprising:
    securing the connecting element to the first and second anchors;
    disconnecting the inserter instrument from the connecting element; and
    moving the inserter instrument in a reverse direction through the arc and thereby removing the inserter instrument from the patient.

5. The method of claim 4, further comprising:
    unmounting the inserter instrument from the first and second anchor extensions; and
    uncoupling the first and second anchor extensions from the first and second anchors.

6. The method of claim 1, wherein the connecting element is positioned through receivers in the anchors after introducing the connecting element.

7. The method of claim 1, further comprising:
    removing through the incision material from an intertransverse space between the first and second bony elements;
    introducing through the incision one or more devices into an intertransverse space between the first and second bony elements;
    engaging first and second anchors to the first and second bony elements after introducing the one or more devices.

8. The method of claim 7, wherein introducing the one or more devices includes introducing one or more interbody fusion devices via a postero-lateral approach to the intertransverse space between adjacent vertebrae.

9. A method of placing a connecting element in a patient, comprising:
    placing first and second anchors in first and second bony elements of the body through an incision in the patient;
    positioning first and second anchor extensions with distal ends removably engaged to respective ones of the first and second anchors so that the first and second anchor extensions extend through the incision to proximal ends of the first and second anchor extensions located outside the patient;
    manipulating the anchor extensions in the incision so that the proximal ends of the anchor extensions are located closer to one another than the distal ends of the anchor extensions engaged to the first and second anchors;
    referencing an elongated connecting element to at least one of the anchor extensions, the connecting element being secured to an installation instrument; and
    moving the installation instrument relative to the at least one anchor extension to position the connecting element from outside the patient into passageways of the first and second anchors in the patient that are located between the first and second anchor extensions and the first and second anchors.

10. The method of claim 9, further comprising referencing the connecting element to each of the first and second anchor extensions.

11. The method of claim 9, further comprising:
    securing the connecting element to the first and second anchors after moving the connecting element into the passageways of the first and second anchors.

12. The method of claim 9, wherein the incision extends generally in the direction of the central axis of the spine for a distance of about 20 millimeters or less.

13. The method of claim 9, wherein the first and second bony elements are first and second vertebrae, respectively.

14. The method of claim 9, wherein the first and second bony elements comprise the same bone.

15. A minimally invasive surgical method, comprising:

making an incision in a patient for accessing first and second bony elements;

placing through the incision first and second anchors, wherein the first and second anchors are configured to be removably coupled to first and second anchor extensions, respectively, wherein the first anchor and the first anchor extension include a first passageway for receiving a connecting element and the second anchor and the second anchor extension include a second passageway for receiving the connecting element;

engaging the first and second anchors to the first and second bony elements, respectively;

referencing a connecting element to a proximal end of at least one of the first and second anchor extensions, the first and second anchor extensions extending through the incision to the proximal end thereof at a location outside the patient;

moving the connecting element relative to the first and second extensions from the proximal ends of the first and second anchor extensions outside the patient to the first and second anchors in the patient;

introducing the connecting element into the passageways of the first and second anchors;

engaging the connecting element in the passageways of the first and second anchors with engaging members received from respective ones of the first and second anchor extensions to the first and second anchors; and removing the first and second anchor extensions from the first and second anchors after engaging the connecting element in the passageways with the engaging members.

16. The method of claim 15, wherein moving the connecting element includes swinging an inserter instrument mounted along a pivot axis to proximal ends of the first and second anchor extensions and moving the connecting element through an arc centered on the pivot axis of the inserter instrument.

17. The method of claim 15, wherein moving the connecting element includes positioning the connecting element percutaneously from a second location to the first and second anchors.

18. The method of claim 15, wherein the incision extends generally in the direction of the central axis of the spine.

19. The method of claim 18, wherein the first and second bony elements are first and second vertebrae, respectively.

20. The method of claim 15, wherein referencing the connecting element includes mounting an inserter instrument to proximal ends of the first and second anchor extensions with the connecting element extending from the inserter instrument.

* * * * *